US012350147B2

(12) United States Patent
Matheny

(10) Patent No.: US 12,350,147 B2
(45) Date of Patent: Jul. 8, 2025

(54) ADAPTABLE PROSTHETIC TISSUE VALVES

(71) Applicant: CorMatrix Cardiovascular, Inc., Roswell, GA (US)

(72) Inventor: Robert G Matheny, Norcross, GA (US)

(73) Assignee: Corvivo Cardiovascular, Inc., Gainesville, FL (US)

(*) Notice: Subject to any disclaimer, the term of this patent is extended or adjusted under 35 U.S.C. 154(b) by 1174 days.

(21) Appl. No.: 17/181,161

(22) Filed: Feb. 22, 2021

(65) Prior Publication Data

US 2021/0169644 A1 Jun. 10, 2021

Related U.S. Application Data

(63) Continuation-in-part of application No. 16/440,504, filed on Jun. 13, 2019, now Pat. No. 11,160,903, and
(Continued)

(51) Int. Cl.
*A61F 2/24* (2006.01)
*A61L 27/36* (2006.01)
(Continued)

(52) U.S. Cl.
CPC .......... *A61F 2/2412* (2013.01); *A61F 2/2418* (2013.01); *A61L 27/3625* (2013.01);
(Continued)

(58) Field of Classification Search
None
See application file for complete search history.

(56) References Cited

U.S. PATENT DOCUMENTS 6,117,979 A 9/2000 Hendriks et al.
9,308,084 B2 4/2016 Matheny
(Continued)

FOREIGN PATENT DOCUMENTS

WO 2014/133539 A1 9/2014
WO 2016/050751 A1 4/2016

OTHER PUBLICATIONS

Extended Search Report, EP Application No. 24153745.5, mailed Apr. 16, 2024.
(Continued)

*Primary Examiner* — Megan Y Wolf
(74) *Attorney, Agent, or Firm* — Thomas | Horstemeyer, LLP

(57) ABSTRACT

Prosthetic valves that include conical shaped base valve members having an annular engagement end, a closed distal end region that restricts fluid flow therethrough, and a plurality of elongated ribbon members, which transition from an open fluid flow configuration to a closed fluid flow configuration in response to expansion and contraction of the base valve member, and a support structure that is configured and adapted to exert retaining forces on the annular engagement ends of the base valve members, whereby the support structure (i) conforms to the shape of the annular engagement ends of the base valve members, (ii) securely positions the annular engagement ends of the base valve members adjacent to and, thereby, in contact with a valve annulus, whereby the annular engagement ends of the base valve members conform to the shape of the valve annulus, and (iii) the annular engagement ends of the base valve members adapt to at least one fluctuation in the configuration and/or dimension of the valve annulus, whereby the annular engagement ends of the base valve members maintain contact therewith.

12 Claims, 17 Drawing Sheets

Related U.S. Application Data a continuation-in-part of application No. 16/129,968, filed on Sep. 13, 2018, now Pat. No. 10,952,843, and a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
*A61L 27/38* (2006.01)
*A61L 27/54* (2006.01)

(52) U.S. Cl.
CPC ....... *A61L 27/3629* (2013.01); *A61L 27/3633* (2013.01); *A61L 27/3641* (2013.01); *A61L 27/3826* (2013.01); *A61L 27/54* (2013.01); *A61F 2230/006* (2013.01); *A61F 2230/0067* (2013.01); *A61L 2300/402* (2013.01); *A61L 2300/406* (2013.01); *A61L 2300/408* (2013.01); *A61L 2300/41* (2013.01); *A61L 2300/416* (2013.01); *A61L 2300/42* (2013.01); *A61L 2430/20* (2013.01)

(56) References Cited

U.S. PATENT DOCUMENTS

| | | | |
|---|---|---|---|
| 10,166,098 | B2 | 1/2019 | Khairkhahan et al. |
| 2009/0088838 | A1 | 4/2009 | Shaolian et al. |
| 2010/0262231 | A1* | 10/2010 | Tuval .................... A61F 2/2409 |
| | | | 623/2.4 |
| 2013/0190860 | A1 | 7/2013 | Sundt, III |
| 2014/0330369 | A1 | 11/2014 | Matheny |
| 2015/0032205 | A1* | 1/2015 | Matheny ................. A61L 27/54 |
| | | | 623/2.15 |
| 2016/0317300 | A1* | 11/2016 | Matheny ................. A61L 27/50 |
| 2017/0086971 | A1* | 3/2017 | Braido .................. A61F 2/2418 |
| 2018/0153686 | A1 | 6/2018 | Matheny |
| 2020/0022808 | A1 | 1/2020 | Matheny |
| 2020/0069840 | A1 | 3/2020 | Matheny |
| 2020/0163761 | A1 | 5/2020 | Hariton et al. |
| 2020/0368178 | A1 | 11/2020 | Naso et al. |

OTHER PUBLICATIONS

Search Report mailed on Oct. 16, 2024 for European Patent Application No. 21926982.6.

Search Report mailed on Oct. 17, 2024 for European Patent Application No. 21926977.6.

* cited by examiner

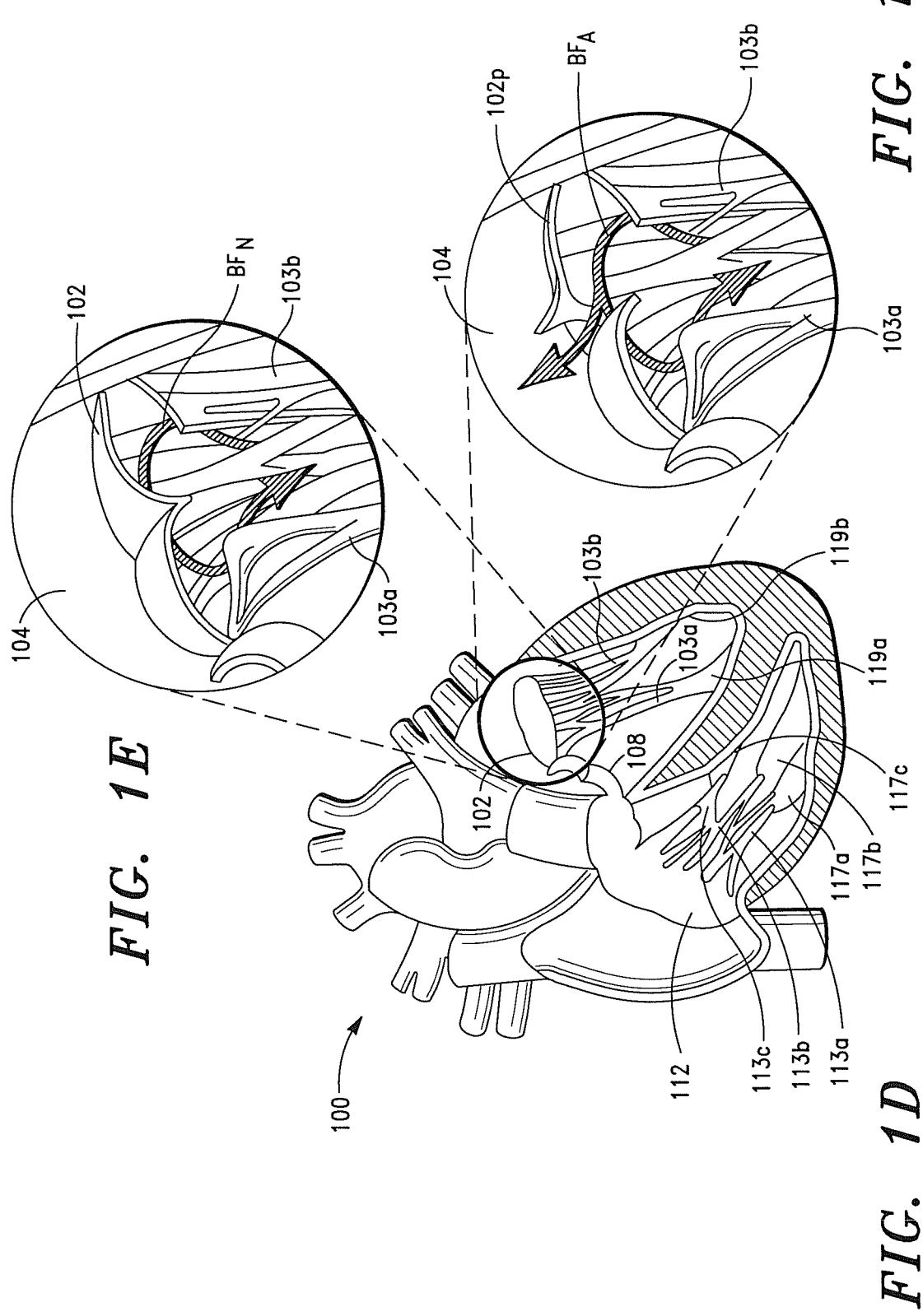

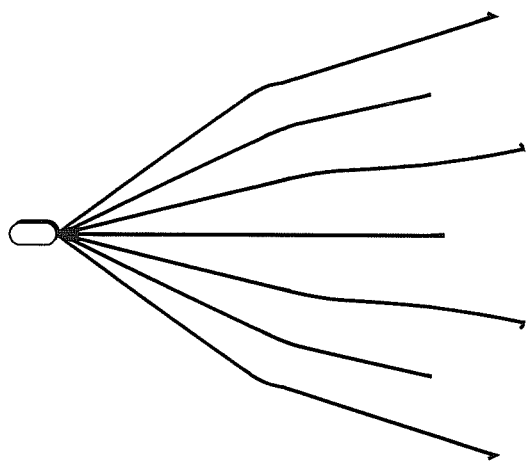
FIG. 6A
FIG. 6B
FIG. 6C
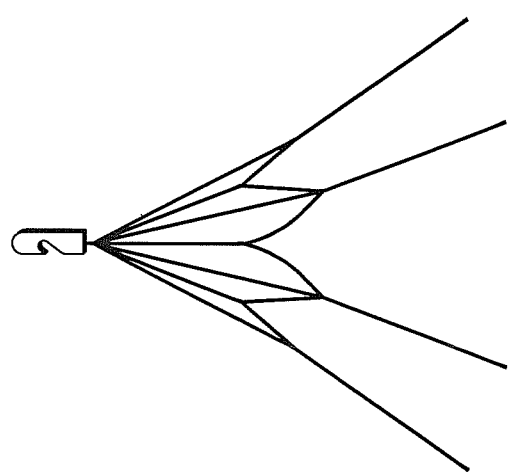
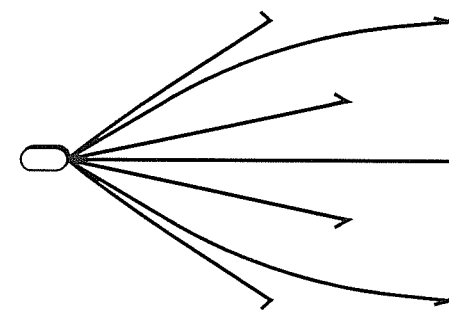
FIG. 6D
FIG. 6E
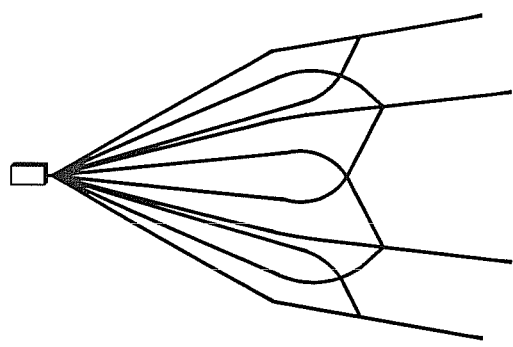

ADAPTABLE PROSTHETIC TISSUE VALVES

CROSS-REFERENCE TO RELATED APPLICATIONS

This application is a continuation-in-part of U.S. application Ser. No. 16/440,504, filed on Jun. 13, 2019, which is a continuation-in-part of U.S. application Ser. No. 16/129,968, filed on Sep. 13, 2018, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to prosthetic valves for replacing defective cardiovascular valves. More particularly, the present invention relates to prosthetic atrioventricular valves and methods for anchoring same to cardiovascular structures and/or tissue.

BACKGROUND OF THE INVENTION

As is well known in the art, the human heart has four valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIGS. 1C and 1D, there are also generally five papillary muscles in the heart 100; three in the right ventricle 116 and two in the left ventricle 106. The anterior, posterior and septal papillary muscles 117a, 117b, 117c of the right ventricle 116 each attach via chordae tendineae 113a, 113b, 113c to the tricuspid valve 112. The anterior and posterior papillary muscles 119a, 119b of the left ventricle 106 attach via chordae tendineae 103a, 103b to the mitral valve 102 (see also FIG. 1E).

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordae or several disease states. Stenosis and insufficiency can also occur concomitantly in the same valve or in different valves.

Both of the noted valve abnormalities can adversely affect organ function and result in heart failure. By way of example, referring first to FIG. 1E, there is shown normal blood flow (denoted "$BF_N$") proximate the mitral valve 102 during closure. Referring now to FIG. 1F, there is shown abnormal blood flow (denoted "$BF_A$") or regurgitation caused by a prolapsed mitral valve 102p. As illustrated in FIG. 1F, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e. "vegetation") on the valve leaflets. The vegetation can, and in many instances will, flake off (i.e. "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize and affect the lungs. The noted embolization can, and in many instances will, result in lung dysfunction.

Treatment of the noted heart valve dysfunctions often requires replacement of the diseased or defective heart valve with a prosthetic heart valve.

Various prosthetic heart valves have thus been developed for replacement of natural diseased or defective heart valves. Illustrative are the tubular prosthetic mammalian tissue valves disclosed in Applicant's U.S. Pat. Nos. 9,044,319, 8,845,719, 8,709,076, 8,790,397, 8,696,744, 8,409,275 and 9,011,526. Further tubular prosthetic valves are disclosed in U.S. Pat. Nos. 8,257,434 and 7,998,196.

A problem that is often encountered with replacing diseased or defective native heart valves with a prosthetic heart valve is obtaining a secure and reliable engagement of the prosthetic heart valves to cardiovascular structures; particularly, a valve annulus.

Various structures and means have thus been developed to provide secure and reliable attachment of remodelable prosthetic valves to a valve annulus.

The most common surgical method that is employed to engage a prosthetic heart valve to a valve annulus comprises suturing the annular engagement end, i.e., proximal end, of the prosthetic valve directly to the valve annulus.

As is well known in the art, there are, however, numerous drawbacks and disadvantages associated with the noted surgical method. A major drawback is the high risk of perivalvular leaks due to ineffective suturing techniques and sizing mis-matches between the annular engagement end of the prosthetic valve and the host valve annulus.

The further surgical method that is often employed to engage a prosthetic heart valve; particularly, a prosthetic heart valve comprising mammalian tissue, to a valve annulus comprises employing an annular ring, e.g., a circular synthetic ring, which, in some instances is disposed on the annular engagement end of the valve, such as described and illustrated in Applicant's U.S. Pat. No. 8,409,275, and suturing the annular engagement end of the valve and associated annular ring directly to the valve annulus.

Although it has been found that such method can, and in most instances will, substantially reduce the risk of perivalvular leaks, as discussed below, since the annular engagement end of the valve and associated annular ring typically comprise a fixed size, several additional issues are presented.

As is well known in the art, a valve annulus can, and many times will, fluctuate in size, e.g., dilated cardiomyopathy, mitral valve regurgitation and Ebstein anomaly. A valve annulus can also be abnormally large or small.

When a fixed annular engagement end of a prosthetic valve is secured to a valve annulus with an abnormal valve annulus size, the size of the annular engagement end is typically adjusted to match the abnormal valve annulus size and, thus, merely accommodates the pathology of the cardiovascular disease or disorder associated with the abnormal valve annulus size.

There are, thus, several significant drawbacks and disadvantages associated with adjusting a fixed annular engagement end of a prosthetic valve to match an abnormal valve annulus size.

A major disadvantage is that when a fixed annular engagement end of a prosthetic valve is sized to match a valve annulus having an abnormally large or small valve annulus size due to a cardiovascular disease or disorder, healing of the valve annulus tissue is often adversely affected.

Further, when the disease or disorder is addressed or managed, the valve annulus often returns to a normal physiologically functional size and the fixed annular engagement end will no longer be able to accommodate the valve annulus. This often necessitates an additional valve replacement procedure to replace the prosthetic valve with an appropriately sized valve.

A similar situation is presented when a prosthetic valve having a fixed annular engagement end is implanted in an infantile, juvenile or adolescent host. As the host ages and the valve annulus size increases, the fixed annular engagement end will no longer be able to accommodate the valve annulus and an additional valve replacement procedure will similarly be necessary to replace the prosthetic valve with an appropriately sized valve.

There is thus a need to provide prosthetic valves that are configured and adapted to: (i) accommodate a broad range of valve annulus configurations and dimensions, (ii) adapt to at least one fluctuation in the configuration and/or dimension of the valve annulus in vivo, whereby, the annular engagement end or region of the valves maintains sealed engagement to the valve annulus, and (iii) significantly decrease or effectively eliminate the incidence of perivalvular leaks.

There is also a need for improved methods for attaching prosthetic valves to cardiovascular structures and/or tissue that significantly decrease or effectively eliminate the incidence of perivalvular leaks.

It is therefore object of the present invention to provide prosthetic valves having an adaptable or dynamic annular engagement end or region that will accommodate a broad range of valve annulus configurations and dimensions, and adapt to at least one fluctuation in the configuration and/or dimension of the valve annulus in vivo, whereby, the annular engagement end or region of the valves maintains sealed engagement to the valve annulus.

It is another object of the present invention to provide improved prosthetic valves that significantly decrease or effectively eliminate the incidence of perivalvular leaks after implant in a subject.

It is another object of the present invention to provide improved methods for attaching prosthetic valves to cardiovascular structures and/or tissue that significantly decrease or effectively eliminate the incidence of perivalvular leaks.

It is another object of the present invention to provide improved prosthetic valves and methods for attaching same to cardiovascular structures and/or tissue that maintain or enhance the structural integrity of the valves when the valves are subjected to cardiac cycle induced stress.

It is another object of the present invention to provide improved prosthetic valves and methods for attaching same to cardiovascular structures and/or tissue that preserve the structural integrity of the cardiovascular structure(s) when attached thereto.

It is another object of the present invention to provide prosthetic valves that remodel, and induce host tissue proliferation, remodeling and regeneration of new tissue and tissue structures with site-specific structural and functional properties when engaged to cardiovascular structures.

It is another object of the present invention to provide prosthetic valves that induce adaptive regeneration when engaged to cardiovascular structures and subjected to cardiac cycle forces.

It is another object of the present invention to provide prosthetic valves that are capable of administering at least one biologically active agent and/or pharmacological agent to host tissue and, thereby produce a desired biological and/or therapeutic effect when disposed proximate the host tissue.

SUMMARY OF THE INVENTION

The present invention is directed to prosthetic valves that can be readily employed to selectively replace diseased or defective heart valves, and methods for attaching (or anchoring) same to cardiovascular structures and/or tissue.

In a preferred embodiment of the invention, the prosthetic valves comprise base valve structures or members, which are formed from a pre-formed sheet structure.

In a preferred embodiment of the invention, the base valve members comprise an annular engagement end, a closed distal end region that restricts fluid flow therethrough, and a plurality of elongated ribbon members.

In a preferred embodiment of the invention, the plurality of elongated ribbon members form a plurality of fluid flow modulating regions, which transition from an open fluid flow configuration to a closed fluid flow configuration in response to expansion and contraction of the base valve member.

In a preferred embodiment of the invention, the prosthetic valves further comprise an internal support structure that is configured and adapted to exert at least one, more preferably, a plurality of retaining forces, on the annular engagement ends of the base valve members and, hence, prosthetic valves formed therewith, whereby the support structure (i) conforms to the annular engagement end of the prosthetic valves, (ii) securely positions the annular engagement ends of the prosthetic valves adjacent to and, thereby, in contact with a target valve annulus, whereby the annular engagement ends of the prosthetic valves conform to the shape of the valve annulus, and (iii) the annular engagement ends of the prosthetic valves adapt to at least one fluctuation in the configuration and/or dimension of the valve annulus, e.g., a mitral valve annulus, whereby the annular engagement ends of the prosthetic valves maintain contact therewith.

In some embodiments of the invention, when the support structure exerts a retaining force on the annular engagement ends of the prosthetic valves, the support structure is further adapted to maintain contact of the annular engagement ends of the prosthetic valves to the valve annulus for a predetermined period of time.

According to the invention, the base valve members and support structures can comprise various biocompatible materials.

In a preferred embodiment of the invention, the base valve members comprise mammalian-based tissue.

In a preferred embodiment, the mammalian-based tissue comprises acellular ECM and, hence, an ECM composition comprising same.

In some embodiments of the invention, the mammalian-based tissue (and, thereby, compositions comprising same) further comprises at least one additional biologically active agent or composition, i.e., an agent that induces or modulates a physiological or biological process, or cellular activity, e.g., induces proliferation, and/or growth and/or regeneration of tissue.

In some embodiments of the invention, the biologically active agent comprises a growth factor, including, without limitation, transforming growth factor beta (TGF-β), fibroblast growth factor-2 (FGF-2), and vascular endothelial growth factor (VEGF).

In some embodiments of the invention, the biologically active agent comprises an exosome.

In some embodiments of the invention, the mammalian-based tissue (and, thereby, compositions comprising same) further comprises at least one pharmacological agent or composition (or drug), i.e., an agent or composition that is capable of producing a desired biological effect in vivo, e.g., stimulation or suppression of apoptosis, stimulation or suppression of an immune response, etc.

In some embodiments of the invention, the pharmacological agent comprises a statin, i.e., a HMG-CoA reductase inhibitor, such as cerivastatin.

In some embodiments of the invention, the pharmacological agent comprises an antibiotic, such as vancomycin and gentamicin.

In some embodiments of the invention, the support structures similarly comprise an ECM composition comprising acellular ECM derived from mammalian tissue.

In some embodiments, the support structures comprise a polymeric composition comprising at least one biocompatible polymer.

In some embodiments, the support structures comprise a biocompatible metal, such as a nickel-titanium alloy and stainless steel.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A-1D are schematic illustrations of a human heart;

FIG. 1E is an illustration of a normal mitral valve;

FIG. 1F is an illustration of a prolapsed mitral valve;

FIGS. 6A-6E are perspective views of further embodiments of adaptive support structures, in accordance with the invention;

DETAILED DESCRIPTION OF THE PREFERRED EMBODIMENT

Figure 1A:
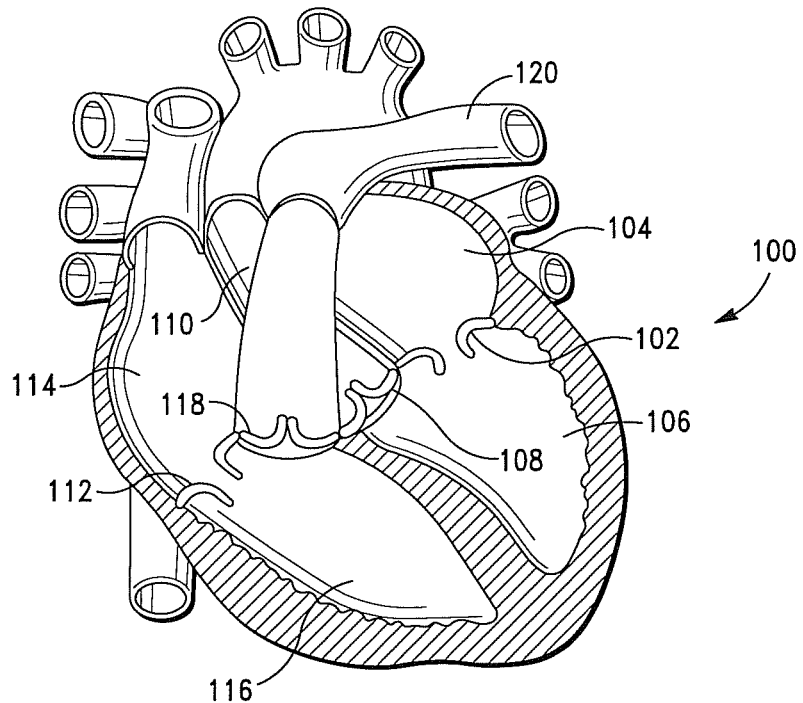
Figure 1B:
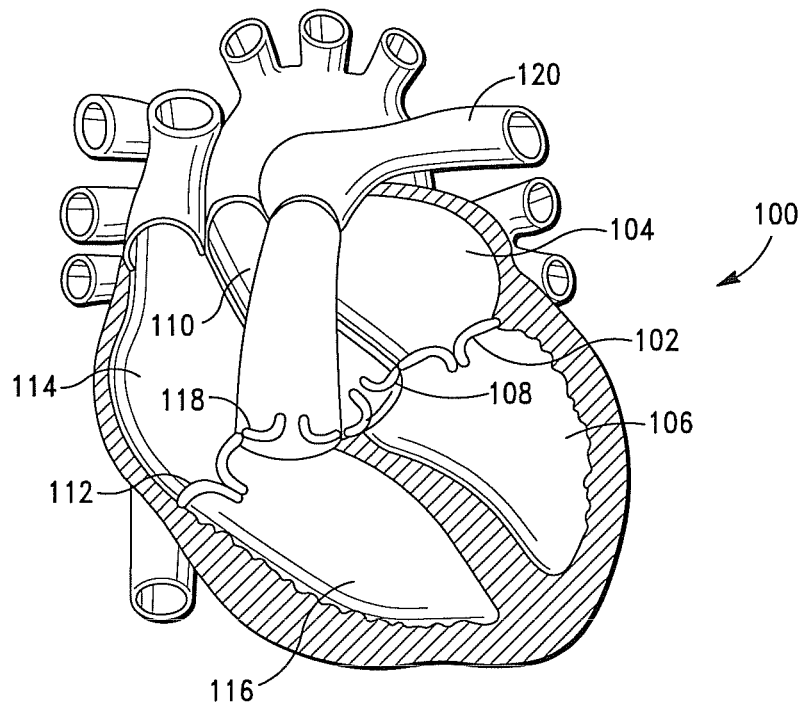
Figure 1C:
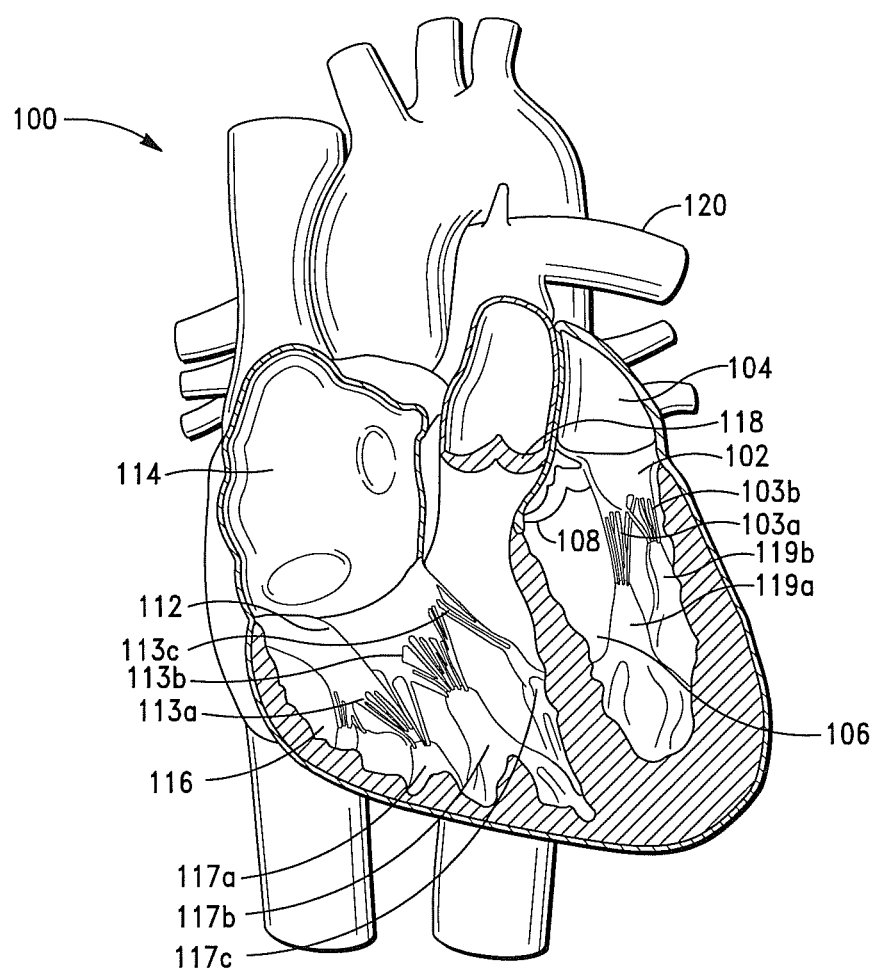

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein are hereby incorporated by reference herein in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means ECM that has a reduced content of cells.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM can also comprise collagen from mammalian sources.

The terms "heart tissue" and "cardiac tissue" are used collectively herein, and mean and include, without limitation, mammalian tissue derived from any cardiovascular structure including, without limitation, pericardial tissue, myocardial tissue, vascular tissue and the like.

The terms "valve annulus" and "valve annulus region" are used collectively herein, and mean and include, without limitation, any physiological structure or region of a living organism that supports a native heart valve or a component thereof.

The terms "mammalian-based tissue", "collagenous mammalian tissue" and "collagenous tissue" are used collectively herein, and mean and include, without limitation, tissue and compositions comprising same that is derived from a mammalian tissue source.

According to the invention, the collagenous mammalian tissue can similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

The collagenous mammalian tissue can also be derived from a mammalian tissue source that is devoid of xenogeneic antigens, including, without limitation, collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetylneuraminic acid hydroxylase, swine leukocyte antigen class I and porcine endogenous retrovirus polymerase (referred to herein as "immune privileged collagenous mammalian tissue").

The term "genetically modified organism", as used herein means and includes any living organism that has at least one gene modified by artificial means, e.g., gene editing.

The term "immune privileged collagenous mammalian tissue", as used herein means and includes xenogeneic collagenous mammalian tissue that can be disposed proximate mammalian tissue with a minimal or virtually absent adverse immune response; particularly, an adverse immune response associated with xenogeneic tissue graft rejection.

According to the invention, the term "mammalian" means and includes, without limitation, wain blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "crosslinked collagenous mammalian tissue", as used herein, means and includes mammalian tissue that exhibits at least 25% chemical bonding of adjacent chains of molecules, i.e., collagen fibrils, which comprise the collagenous mammalian tissue.

The term "polymer", as used herein means and includes, without limitation, polyurethane urea, porous polyurethane urea (Artelon®), polypropylene, poly(s-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™) and polyethylene terephthalate (Dacron™), and combinations thereof.

The term "natural polymer", as used herein means and includes, without limitation, polysaccharides (e.g., starch and cellulose), proteins (e.g., gelatin, casein, silk, wool, etc.), and polyesters (e.g., polyhydroxyalkanoates).

The term "biologically active agent", as used herein, means and includes an agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β) and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes an exosome and/or microsome.

The terms "exosome" and "microsome" as used herein mean and include a lipid bilayer structure that contains or encapsulates a biologically active agent and/or pharmacological agent, including, without limitation, a growth factor, e.g., TGF-β, TGF-α, VEGF and insulin-like growth factor (IGF-1), a cytokine, e.g., interleukin-10 (IL-10), a transcription factor and microRNA (miRNA).

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oxytetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the Class I-Class V antiarrhythmic agents disclosed in Applicant's U.S. Pat. Nos. 9,119,841, 10,188,509, 10,188,510 and 10,143,778, and Co-pending application Ser. Nos. 16/129,968 and 16/990,236, including, without limitation, (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the antibiotics disclosed in Applicant's U.S. Pat. Nos. 9,119,841, 10,188,509, 10,188,510 and 10,143,778, and Co-pending application Ser. Nos. 16/129,968 and 16/990,236, including, without limitation, aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

The terms "anti-inflammatory" and "anti-inflammatory agent" thus include the anti-inflammatories disclosed in Applicant's U.S. Pat. Nos. 9,119,841, 10,188,509, 10,188,510 and 10,143,778, and Co-pending application Ser. Nos. 16/129,968 and 16/990,236, including, without limitation, desoximetasone, dexamethasone dipropionate, cloticasone propionate, diftalone, fluorometholone acetate, fluquazone, meseclazone, mesterolone, methandrostenolone, methenolone, methenolone acetate, methylprednisolone suleptanate, halopredone acetate, alclometasone dipropionate, apazone, balsalazide disodium, cintazone cormethasone acetate, cortodoxone, diflorasone diacetate, diflumidone sodium, endrysone, fenpipalone, flazalone, fluretofen, fluticasone propionate, isoflupredone acetate, nabumetone, nandrolone, nimazone, oxyphenbutazone, oxymetholone, phenbutazone, pirfenidone, prifelone, proquazone, rimexolone, seclazone, tebufelone and testosterone.

The terms "pharmacological agent", "active agent" and "drug" also mean and include the statins, i.e., HMG-CoA reductase inhibitors, disclosed in Applicant's U.S. Pat. Nos. 9,119,841, 10,188,509, 10,188,510 and 10,143,778, and Co-pending application Ser. Nos. 16/129,968 and 16/990,236, including, without limitation, atorvastatin, cerivastatin, fluvastatin and lovastatin.

The terms "pharmacological agent", "active agent", "drug" and "active agent formulation" further mean and include the anti-proliferative agents disclosed in Applicant's U.S. Pat. Nos. 9,119,841, 10,188,509, 10,188,510 and 10,143,778, and Co-pending application Ser. Nos. 16/129,968 and 16/990,236, including, without limitation, paclitaxel, sirolimus and derivatives thereof, including everolimus.

The term "pharmacological composition", as used herein, means and includes a composition comprising a "pharmacological agent" and/or any additional agent or component identified herein.

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The term "comprise" and variations of the term, such as "comprising" and "comprises," as used in connection with the a prosthetic valve composition and/or mammalian tissue, also means a composition and/or mammalian tissue employed to form a prosthetic valve structure, such as a sheet member, and, hence, a prosthetic valve of the invention.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to prosthetic valves that can be readily employed to selectively replace diseased or defective heart valves, and methods for attaching (or anchoring) same to cardiovascular structures and/or tissue.

As discussed in detail below, in a preferred embodiment of the invention, the prosthetic valves comprise base valve structures or members, which are formed from pre-formed sheet structures.

In a preferred embodiment of the invention, the base valve members comprise seamless base valve members.

In a preferred embodiment of the invention, the base valve members further comprise an annular engagement end, a closed distal end region that restricts fluid flow therethrough, and a plurality of elongated ribbon members (referred to hereinafter as "base 'ribbon structure' valve members").

In a preferred embodiment of the invention, the plurality of elongated ribbon members form a plurality of fluid flow modulating regions, which transition from an open fluid flow configuration to a closed fluid flow configuration in response to expansion and contraction of the base valve member.

As indicated above and discussed in detail below, in a preferred embodiment of the invention, the prosthetic valves further comprise a support structure that is configured and adapted to exert at least one, more preferably, a plurality of retaining forces, on the annular engagement ends of the base valve members and, hence, prosthetic valves formed therewith, whereby the support structure (i) conforms to the annular engagement end of the prosthetic valves, (ii) securely positions the annular engagement ends of the prosthetic valves adjacent to and, thereby, in contact with a target valve annulus valve, whereby the annular engagement ends of the prosthetic valves conform to the shape of the valve annulus, and (iii) the annular engagement ends of the prosthetic valves adapt to at least one fluctuation in the configuration and/or dimension of the valve annulus, e.g., a mitral valve annulus, whereby the annular engagement ends of the prosthetic valves maintain contact therewith.

In some embodiments of the invention, when the support structure exerts a retaining force on the annular engagement ends of the prosthetic valves, the support structure is further adapted to maintain contact of the annular engagement ends of the prosthetic valves to the valve annulus for a predetermined period of time.

In some embodiments, the retaining force that is exerted by the support structure is in the range of approximately 0.2 to 0.5 lbs.

As discussed in detail below, in a preferred embodiment of the invention, the support structure comprises an adaptive support structure.

In some embodiments of the invention, the support structure comprises an annular ring that is disposed proximate the annular engagement end of the prosthetic valves.

In some embodiments of the invention, the annular ring comprises a microneedle anchoring mechanism that is further configured and adapted to engage the annular engagement end of the prosthetic valves, protrude through the annular engagement end of the prosthetic valves, engage cardiovascular tissue of a valve annulus (or other cardiovascular structure) and, thereby, position the prosthetic valve proximate the valve annulus.

Suitable anchoring mechanisms are disclosed in Applicant's U.S. Pat. Nos. 9,044,319, 10,188,509, 10,188,510 and 10,052,409, and U.S. application Ser. Nos. 16/193,669, 16/238,730 and 16/553,570, which are incorporated by reference herein in their entirety.

In some embodiments of the invention, the closed distal end region of the prosthetic valves comprises a structural ring that preferably enhances the structural integrity of the closed distal end region.

According to the invention, the prosthetic valves of the invention can further comprise a supplemental support structure, such as also disclosed in Applicant's U.S. Pat. Nos. 10,188,510 and 10,052,409, and/or a stent structure, such as described in Applicant's U.S. Pat. No. 10,188,513, which are also incorporated by reference herein.

According to the invention, the base "ribbon structure" valve members and/or support structures and/or annular rings and/or structural rings and/or supplemental support structures of the invention can comprise various biocompatible materials and compositions formed therefrom.

In some embodiments of the invention, the base "ribbon structure" valve members comprise mammalian-based tissue.

As indicated above, in a preferred embodiment of the invention, the mammalian-based tissue comprises acellular ECM (and, hence, ECM compositions comprising same) derived from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508; which are incorporated by reference herein in their entirety.

The mammalian tissue sources include, without limitation, the small intestine, large intestine, stomach, lung, liver, kidney, pancreas, peritoneum, placenta, heart, bladder, prostate, tissue surrounding growing enamel, tissue surrounding growing bone, and any fetal tissue from any mammalian organ.

The mammalian tissue sources can thus comprise, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, placental tissue, omentum tissue, cardiac tissue, kidney tissue, pancreas tissue, lung tissue, and combinations thereof. The ECM can also comprise collagen from mammalian sources.

According to the invention, the ECM can also be derived from the same or different mammalian tissue sources, as disclosed in U.S. application Ser. Nos. 13/033,053 and 13/033,102, now U.S. Pat. No. 8,758,448; which are incorporated by reference herein.

In a preferred embodiment of the invention, the ECM comprises sterilized and decellularized ECM.

According to the invention, the ECM can be sterilized and decellularized by various conventional means.

In some embodiments of the invention, the ECM is sterilized and decellularized via applicant's proprietary process disclosed in U.S. application Ser. No. 13/480,205 and U.S. Pat. Nos. 9,060,969 and 9,446,078; which are expressly incorporated by reference herein in their entirety.

It is thus contemplated that, following placement of a base "ribbon structure" valve member comprising an ECM composition, i.e., acellular ECM, (and, hence, a prosthetic "ribbon structure" valve of the invention formed therewith) on or in a cardiovascular structure (or structures) of a subject, e.g., valve annulus, and, hence, proximate damaged cardiovascular tissue associated therewith, the base "ribbon structure" valve member will become populated with endogenous cells that will gradually remodel the base valve member, i.e., ECM tissue thereof, into cardiovascular tissue and tissue (and, hence, valve) structures.

It is further contemplated that, following placement of a base "ribbon structure" valve member comprising an ECM composition, i.e., acellular ECM, (and, hence, a prosthetic "ribbon structure" valve of the invention formed therewith) on or in a cardiovascular structure (or structures) of a subject, and, hence, proximate damaged cardiovascular tissue associated therewith, stem cells will migrate to the base "ribbon structure" valve member, i.e., ECM tissue thereof, from the point(s) at which the base "ribbon structure" valve member is attached to the cardiovascular structure or structures.

It is still further contemplated that, during circulation of epithelial and endothelial progenitor cells after placement of a base "ribbon structure" valve member comprising an ECM composition comprising acellular ECM (and, hence, a prosthetic "ribbon structure" valve of the invention formed therewith) on a cardiovascular structure (or structures), the surfaces of the base "ribbon structure" valve member, i.e., ECM tissue thereof, will rapidly become lined or covered with epithelial and/or endothelial progenitor cells.

It is still further contemplated that the points at which abase "ribbon structure" valve member comprising an ECM composition (and, hence, a prosthetic "ribbon structure" valve of the invention formed therewith) is attached to a cardiovascular structure (or structures) in a subject will serve as points of constraint that direct remodeling of the ECM into cardiovascular tissue and valve structures that are identical or substantially identical to properly functioning native cardiovascular tissue and valve structures.

According to the invention, the mammalian-based tissue can further comprise collagenous mammalian tissue derived from a mammalian tissue source.

According to the invention, the collagenous mammalian tissue can be similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

In some embodiments of the invention, the collagenous mammalian tissue comprises pericardium tissue.

In some embodiments of the invention, the mammalian tissue source comprises a bovine tissue source, e.g., bovine pericardium tissue.

In some embodiments of the invention, the mammalian tissue source comprises a porcine tissue source, e.g., porcine pericardium tissue.

In some embodiments, the collagenous mammalian tissue comprises crosslinked collagenous mammalian tissue.

In some embodiments of the invention, the collagenous mammalian tissue is derived from a mammalian tissue source that is devoid of xenogeneic antigens.

In some embodiments, the collagenous mammalian tissue thus comprises collagenous mammalian tissue that is devoid of one of the following xenogeneic antigens: galactose-alpha-1,3-galactose (also referred to as α-gal), beta-1,4 N-acetylgalactosaminyl-transferase 2, membrane cofactor protein, hepatic lectin H1, cytidine monophospho-N-acetylneuraminic acid hydroxylase, swine leukocyte antigen class I and porcine endogenous retrovirus polymerase (referred to hereinafter as "immune privileged collagenous mammalian tissue").

In some embodiments, the immune privileged collagenous mammalian tissue is derived from a genetically modified organism, such as, by way of example, a genetically modified pig and/or bovine.

In some embodiments, the immune privileged collagenous mammalian tissue is thus derived from a genetically modified pig.

In some embodiments, the genetically modified pig comprises a pig originating from at least one porcine germline cell, e.g., embryo, that has been genetically altered or reconstructed to knockout or delete at least one porcine gene that encodes for a xenogeneic antigen product.

According to the invention, the genetic alteration or reconstruction of a germline cell; more specifically, a porcine embryo can be done according to any conventional gene editing method, such as conventional gene editing methods that employ clustered regularly interspaced short palindromic repeats (CRISPR)-Cas9, Transcription Activator-like Effector Nucleases (TALEN) or RNA interference.

In some embodiments, the knockout or deletion of a gene in a porcine embryo and, hence, pig developed therefrom is done according to the CRISPR-Cas9 gene editing method described in Niu, et al., *Inactivation of Porcine Endogenous Retrovirus in Pigs Using CRISPR-Cas9*, Science, vol. 357, no. 6357, pp. 1303-1307 (2017), which is incorporated by reference herein in its entirety.

According to the invention, the noted gene editing methods can be adapted and configured to knockout or delete any genes in a porcine embryo that encode for xenogeneic antigens including, without limitation, GGTA1 (galactose-alpha-1,3-galactose), β4GalNT2 (beta-1,4 N-acetylgalactosaminyltransferase 2), CD46 (membrane cofactor protein), ASGR1 (hepatic lectin H1), CMAH (cytidine monophospho-N-acetylneuraminic acid hydroxylase), SLA class I (swine leukocyte antigen class I) and PERV pol (porcine endogenous retrovirus polymerase) gene.

In some embodiments, the collagenous mammalian tissue is derived from mammalian tissue of a pig developed from an embryo that has been genetically altered by knocking out or deleting the genes GGTA1, β4GalNT2 and CMAH, which encode for the xenogeneic antigen products galactose-alpha-1,3-galactose, beta-1,4 N-acetylgalactosaminyl-transferase 2 and cytidine monophospho-N-acetylneuraminic acid hydroxylase, respectively.

According to the invention, the likelihood of inducing an adverse immune response, including adverse immune responses associated with xenogeneic tissue graft rejection, in vivo with the above referenced immune privileged collagenous mammalian tissue is minimal.

In some embodiments of the invention, the prosthetic valves of the invention are formed from and, hence, comprise a polymeric composition comprising at least one polymer; preferably, a biocompatible polymer.

According to the invention, suitable biocompatible polymers include, without limitation, polyurethane urea, including porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™), and polyethylene terephthalate (Dacron™), and combinations thereof.

In some embodiments of the invention, the mammalian-based tissue (and compositions comprising same) and/or polymeric composition further comprises at least one additional biologically active agent or composition, i.e., an agent that induces or modulates a physiological or biological process, or cellular activity, e.g., induces proliferation, and/or growth and/or regeneration of tissue.

According to the invention, suitable biologically active agents include any of the aforementioned biologically active agents, and agents set forth in Applicant's U.S. Pat. No. 10,188,510 and U.S. application Ser. No. 15/877,803, which are incorporated by reference herein.

As indicated above, in some embodiments of the invention, the biologically active agent comprises a growth factor, including, without limitation, transforming growth factor beta (TGF-β), fibroblast growth factor-2 (FGF-2) (also referred to as basic fibroblast growth factor (bFGF)), and vascular endothelial growth factor (VEGF).

In some embodiments of the invention, the mammalian-based tissue (and compositions comprising same) and/or polymeric composition further comprises at least one pharmacological agent or composition (or drug), i.e., an agent or composition that is capable of producing a desired biological effect in vivo, e.g., stimulation or suppression of apoptosis, stimulation or suppression of an immune response, etc.

According to the invention, suitable pharmacological agents and compositions include any of the aforementioned pharmacological agents and agents set forth in Applicant's U.S. Pat. No. 10,188,510 and U.S. application Ser. No. 15/877,803.

In some embodiments of the invention, it is thus contemplated that, following placement of a base "ribbon structure" valve member (and, hence, a prosthetic "ribbon structure" valve of the invention formed therewith) on or in a cardiovascular structure (or structures) in a subject and, hence, proximate cardiovascular tissue associated therewith, the base "ribbon structure" valve member (and, hence, a prosthetic "ribbon structure" valve of the invention formed therewith) will induce "modulated healing" of the cardiovascular structure(s) and cardiovascular tissue associated therewith.

The term "modulated healing", as used herein, and variants of this language generally refer to the modulation (e.g., alteration, delay and retardation) of a process involving different cascades or sequences of naturally occurring tissue repair in response to localized tissue damage or injury, substantially reducing their inflammatory effect.

Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments of the invention, a base "ribbon structure" valve member of the invention (and, hence, a prosthetic "ribbon structure" valve of the invention formed therewith) is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments, "modulated healing" means and includes the ability of a base "ribbon structure" valve member of the invention (and, hence, a prosthetic "ribbon structure" valve of the invention formed therewith) to restrict the expression of inflammatory components. By way of example, according to the invention, when a base "ribbon structure" valve member of the invention comprises a statin augmented ECM composition, i.e., a composition comprising ECM and a statin, and the base "ribbon structure" valve member is positioned proximate damaged biological tissue, e.g., attached to a valve annulus, the base "ribbon structure" valve member will restrict expression of monocyte chemoattractant protein-1 (MCP-1) and chemokine (C—C) motif ligand 2 (CCR2).

In some embodiments of the invention, "modulated healing" means and includes the ability of a base "ribbon structure" valve member of the invention, such as, for example, a base "ribbon structure" valve member comprising an antibiotic augmented polymeric composition, to alter a substantial inflammatory phase (e.g., platelet or fibrin deposition) at the beginning of the tissue healing process.

As used herein, the phrase "alter a substantial inflammatory phase" refers to the ability of a base "ribbon structure" valve member of the invention (and, hence, a prosthetic "ribbon structure" valve of the invention formed therewith) to substantially reduce the inflammatory response at a damaged tissue site, e.g., valve annulus, when in contact with tissue at the site.

In such an instance, a minor amount of inflammation may ensue in response to tissue injury, but this level of inflammation response, e.g., platelet and/or fibrin deposition, is substantially reduced when compared to inflammation that takes place in the absence of a prosthetic valve of the invention.

The term "modulated healing" also refers to the ability of a base "ribbon structure" valve member of the invention, particularly, a base "ribbon structure" valve member comprising an ECM composition, to induce host tissue proliferation, bioremodeling, including neovascularization, e.g., vasculogenesis, angiogenesis, and intussusception, and regeneration of new tissue and tissue structures with site-specific structural and functional properties, when disposed proximate damaged tissue of a cardiovascular structure, e.g., a valve annulus.

Thus, in some embodiments of the invention, the term "modulated healing" means and includes the ability of a base "ribbon structure" valve member of the invention (and, hence, a prosthetic "ribbon structure" valve of the invention formed therewith) to modulate inflammation and induce host tissue proliferation and remodeling, and regeneration of new tissue when disposed proximate damaged tissue.

In some embodiments of the invention, the biologically active agent specifically comprises an exosome.

As discussed in detail in Applicant's U.S. application Ser. No. 15/386,640, now U.S. Pat. No. 10,143,778, which is incorporated by reference herein, exosomes significantly enhance the modulated healing induced by the base "ribbon structure" valve members of the invention (and, hence, prosthetic "ribbon structure" valves of the invention formed therewith); particularly, base "ribbon structure" valve members comprising an ECM composition, through several properties/capabilities.

A first seminal property is the capacity of exosomes to generate and provide an exosome lipid bilayer that shields bioactive molecules, e.g., biologically active agents, from proteolytic agents, which can, and often will, degrade unshielded (or free) bioactive molecules and render the molecules non-functional in biological tissue environments.

Exosomes also facilitate and enhance direct interaction by and between bioactive molecules; particularly, biologically active agents and endogenous cells (and, hence, direct delivery of bioactive molecules to endogenous cells) in biological tissue, which enhances the bioactivity of the agents.

Thus, it is contemplated that, in some embodiments of the invention, following placement of a prosthetic "ribbon structure" valve of the invention; particularly, a prosthetic "ribbon structure" valve comprising a base "ribbon structure" valve member comprising exogenously added exosomes, on or in a cardiovascular structure (or structures) of a subject, e.g., valve annulus, and, hence, proximate damaged cardiovascular tissue associated therewith, the prosthetic "ribbon structure" valve will induce a multitude of significant biological processes in vivo, including significantly enhanced inflammation modulation of the cardiovascular tissue, and significantly induced neovascularization, stem cell proliferation, remodeling of the cardiovascular tissue, and regeneration of new tissue and tissue structures.

By way of example, when a base "ribbon structure" valve member comprises an exosome augmented ECM composition comprising encapsulated IL-8 and the base "ribbon structure" valve member and, hence, prosthetic "ribbon structure" valve formed therefrom, is disposed proximate damaged cardiovascular tissue, the prosthetic "ribbon structure" valve will modulate the transition of M1 type "acute inflammatory" macrophages to M2 type "wound healing" macrophages initiated by the acellular ECM.

Byway of further example, when abase "ribbon structure" valve member comprises an exosome augmented ECM composition comprising encapsulated miRNAs, and the base "ribbon structure" valve member and, hence, prosthetic "ribbon structure" valve formed therefrom, is disposed proximate damaged cardiovascular tissue, the prosthetic "ribbon structure" valve will induce enhanced stem cell proliferation via the delivery of exosome encapsulated miRNAs and transcription factors to the damaged cardiovascular tissue, which signals the endogenous stem cells to bind and/or attach to the acellular ECM and proliferate.

In some embodiments of the invention, the support structures and/or annular rings and/or structural rings and/or supplemental support structures comprise one of the aforementioned mammalian-based tissues and/or compositions comprising same.

In some embodiments of the invention, the support structures and/or annular rings and/or structural rings and/or supplemental support structures comprise one of the aforementioned biocompatible polymers and/or polymeric compositions comprising same.

According to the invention, the polymeric composition can further comprise a natural polymer, including, without limitation, polysaccharides (e.g., starch and cellulose), proteins (e.g., gelatin, casein, silk, wool, etc.), and polyesters (e.g., polyhydroxyalkanoates).

In some embodiments, the polymeric composition comprises a cross-linked ECM derived from any one of the aforementioned mammalian tissue sources.

In some embodiments, the polymeric composition comprises a glutaraldehyde cross-linked ECM.

According to the invention, the polymeric composition can further comprise a non-biodegradable polymer, including, without limitation, polytetrafluoroethylene (Teflon®) and polyethylene terephthalate (Dacron®).

In some embodiments, the polymeric composition comprises at least one of the aforementioned biologically active agents and/or pharmacologically active agents.

Thus, in some embodiments of the invention, the support structures and/or annular rings and/or structural rings and/or supplemental support structures similarly have the capacity to induce "modulated healing" of cardiovascular structures and tissue associated therewith.

In some embodiments of the invention, the support structures and/or annular rings and/or structural rings and/or supplemental support structures comprise a biocompatible metal.

According to the invention, suitable metals can comprise, without limitation, nickel-titanium alloy, such as Nitinol®, stainless steel and magnesium.

Figure 2A:
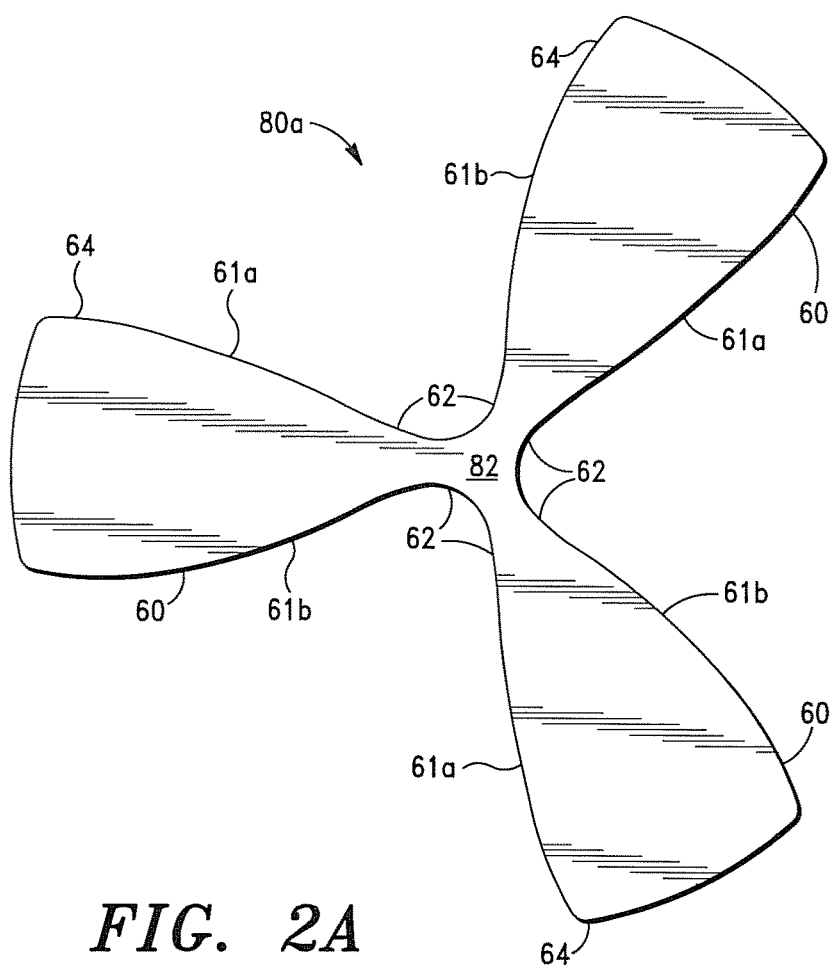
FIG. 2A is a top plan view of one embodiment of a base "ribbon structure" valve member in a pre-formed configuration, in accordance with the invention.
Figure 2B:
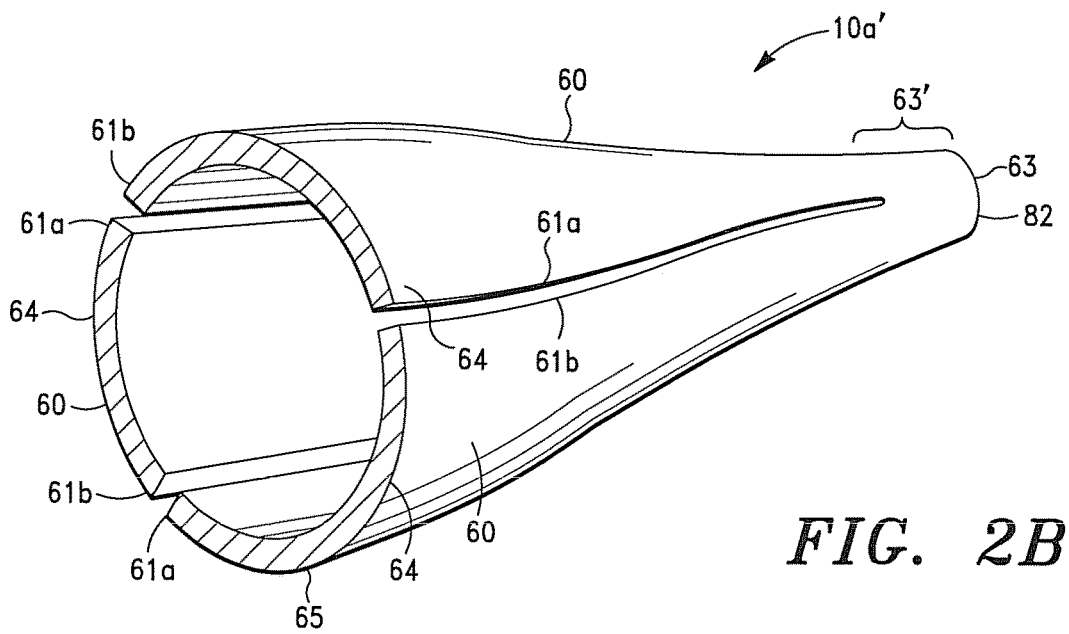
FIG. 2B is a perspective view of the base "ribbon structure" valve member shown in FIG. 2A in a further pre-formed configuration, in accordance with the invention.
Figure 2C:
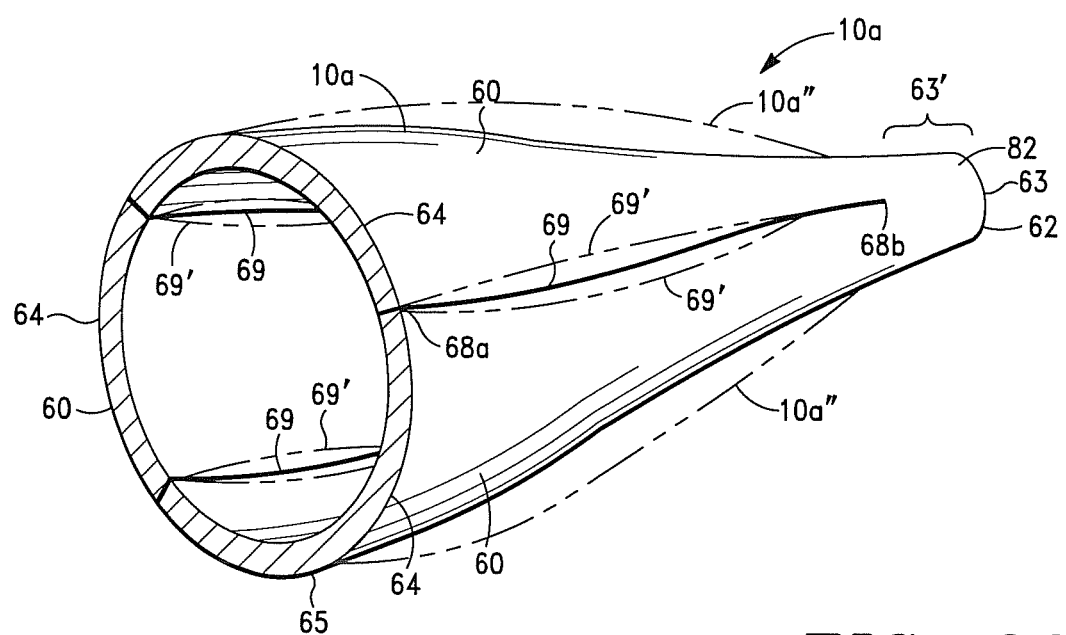
FIG. 2C is a perspective view of the base "ribbon structure" valve member shown in FIGS. 2A and 2B in a formed operational configuration, i.e., a formed prosthetic "ribbon structure" valve, in accordance with the invention.

Referring now to FIGS. 2A-2C, one embodiment of a base "ribbon structure" valve member of the invention, and method for forming same, will be described.

As indicated above, in a preferred embodiment of the invention, the base "ribbon structure" valve member comprises a plurality of elongated ribbon members, such as described in Applicant's Co-pending U.S. application Ser. No. 16/440,504, which is incorporated by reference herein.

A seminal feature of base "ribbon structure" valve members of the invention is that the base "ribbon structure" valve members are formed from and, hence, comprise a seamless pre-formed (or pre-cut) sheet structure.

As set forth in Applicant's Co-pending U.S. application Ser. No. 16/440,504, the base "ribbon structure" valve members can be formed from a single sheet member or multiple sheet members, such as base "ribbon structure" valve member 10f discussed below.

Referring now to FIG. 2A, there is shown one embodiment of a pre-formed sheet member 80a that can be formed into seamless base "ribbon structure" valve members of the invention.

As illustrated in FIG. 2A, the sheet member 80a comprises a central region 82 and a plurality of elongated ribbon members 60, which extend from the central region 82. According to the invention, the ribbon members 60 can comprise any length and shape. The ribbon members 60 can also comprise various widths proximate the proximal end 64.

Referring now to FIGS. 2B and 2C, the base "ribbon structure" valve member 10a is preferably formed by folding each of the elongated ribbon members 60 inwardly to form pre-formed valve structure 10a' that is shown in FIG. 2B, wherein the central region 82 of the sheet member 80a is disposed at the distal end 63 of base "ribbon structure" valve member 10a' and forms a closed distal valve region 63' that restricts fluid flow therethrough, and the first edge regions 61a and the second edge regions 61b of the ribbon members 60 are positioned adjacent each other and, as illustrated in FIG. 2C, in the fully formed (or operational configuration) of base "ribbon structure" valve member 10a, form a plurality of fluid flow modulating regions 69 having proximal and distal ends 68a, 68b.

In a preferred embodiment, the length of each flow modulating region 69 is in the range of approximately 5-99% of the length of the base "ribbon structure" valve member 10a, i.e., distance from the annular engagement end 65 to the distal end 63 of the base "ribbon structure" valve member 10a. More preferably, the length of each flow modulating region 69 is in the range of approximately 10-90% of the length of the base "ribbon structure" valve member 10a.

As further illustrated in FIG. 2C, the proximal ends 64 of ribbon members 60 are also preferably positioned circumferentially about the annular engagement end 65 of the base "ribbon structure" valve member 10a, wherein the base "ribbon structure" valve member 10a, when fully formed operational configuration, comprises a substantially conical shaped base "ribbon structure" valve member.

As set forth in Applicant's Co-pending U.S. application Ser. No. 16/440,504, the base "ribbon structure" valve member 10a is configured to expand during fluid flow through the base "ribbon structure" valve member 10a that comprises a first fluid flow pressure, as shown in phantom in FIG. 2C (denoted 10a"), and contract when the fluid through the base "ribbon structure" valve member 10a comprises a second fluid flow pressure, the second fluid flow pressure being lower than the first fluid flow pressure.

As also set forth in Applicant's Co-pending U.S. application Ser. No. 16/440,504, the fluid flow modulating regions 69 are preferably configured to open during expansion of the base "ribbon structure" valve member 10a, as shown in phantom in FIG. 2C and denoted 69', i.e., the first and second edge regions 61a, 61b separate, wherein the fluid flow is allowed to be transmitted through the fluid flow modulating regions 69, and close during the contraction of the base "ribbon structure" valve member 10a, wherein the fluid flow through base "ribbon structure" valve member 10a is restricted.

According to the invention, the base "ribbon structure" valve member 10a can comprise any number of ribbon members 60. As illustrated in FIGS. 2A-2C, in some embodiments of the invention, the base "ribbon structure" valve member 10a has three (3) equally spaced ribbon members 60.

Referring now to FIGS. 3A-3H, several embodiments of prosthetic "ribbon structure" valves of the invention and methods for forming same will be described in detail.

Figure 3A:
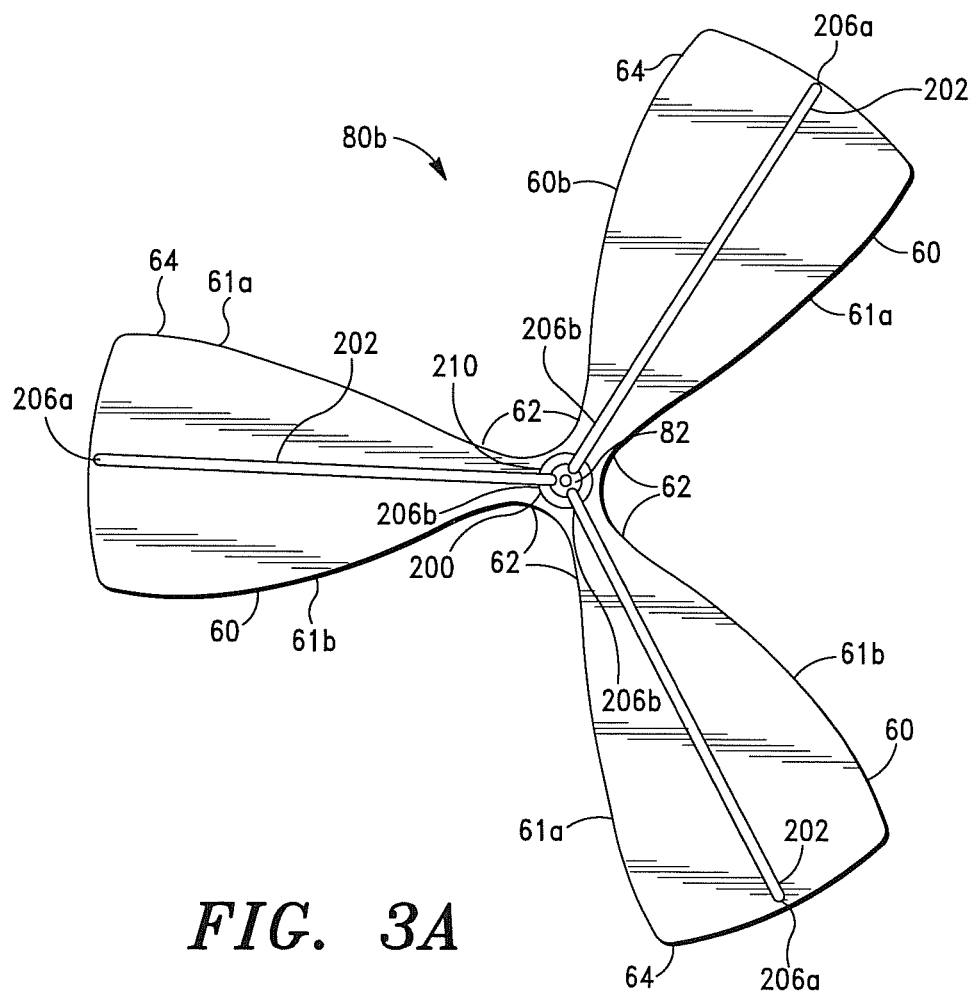
FIG. 3A is a top plan view of a further embodiment of a base "ribbon structure" valve member having one embodiment of an adaptive support structure associated therewith in a pre-formed configuration, in accordance with the invention.
Figure 3B:
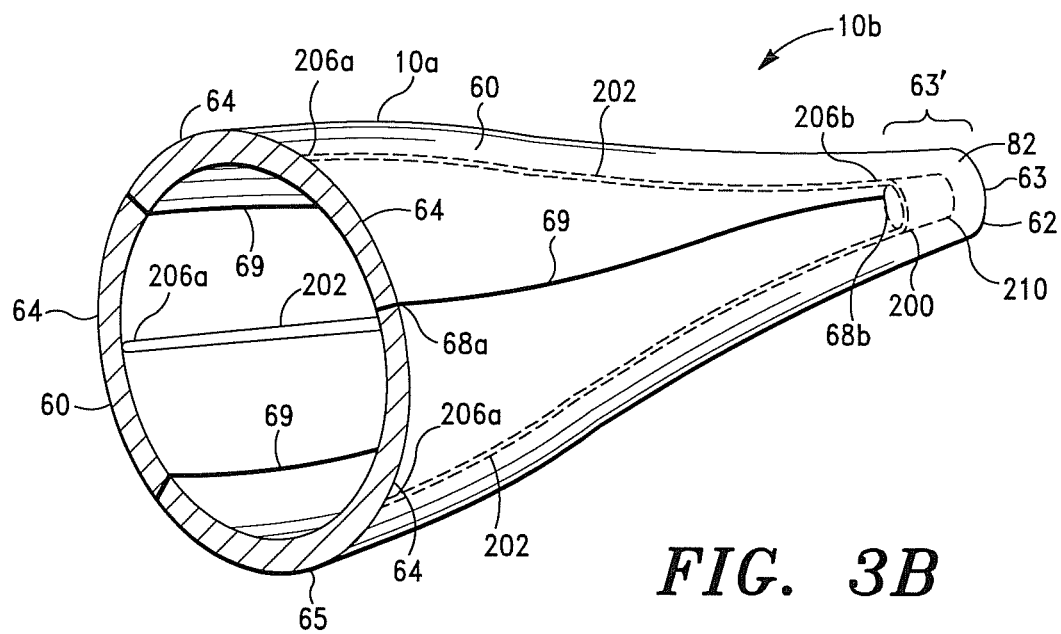
FIG. 3B is a perspective view of the base "ribbon structure" valve member shown in FIG. 3A in a formed operational configuration, i.e., a formed prosthetic "ribbon structure" valve having the embodiment of the adaptive support structure shown in FIG. 3A associated therewith, in accordance with the invention.

Referring first to FIG. 3B, there is shown one embodiment of a prosthetic "ribbon structure" valve of the invention, denoted 10b. As illustrated in FIG. 3B, the prosthetic "ribbon structure" valve 10b comprises conical shaped base "ribbon structure" valve member 10a and adaptive support structure 200.

According to the invention, the prosthetic "ribbon structure" valve 10b is formed from a seamless pre-formed (or pre-cut) sheet member that is similar to sheet member 80a shown in FIG. 2A. However, as illustrated in FIG. 3A, in this instance, the pre-formed sheet member 80b now includes adaptive support structure 200, which is operatively positioned thereon.

As further illustrated in FIG. 3A, the sheet member 80b similarly comprises a central region 82 and a plurality of elongated ribbon members 60 having proximal and distal ends 64, 62, which extend from the central region 82.

According to the invention, the prosthetic "ribbon structure" valve 10b is similarly formed by folding each of the elongated ribbon members 60 of sheet member 80b and the elongated support members 202 of the adaptive support structure 200 associated therewith inwardly, wherein, as illustrated in FIG. 3B, the central region 82 of the sheet member 80a is disposed proximate the distal end 63 of prosthetic valve 10b and forms a closed distal valve region 63' that restricts fluid flow therethrough, and the first edge regions 61a and the second edge regions 61b of the ribbon members 60 are similarly positioned adjacent each other and form the plurality of fluid flow modulating regions 69.

As further illustrated in FIG. 3B, the adaptive support structure 200 preferably comprises a support structure base 210 and a plurality of elongated support members 202 having proximal and distal ends 206a, 206b.

As also illustrated in FIG. 3B, the proximal ends 206a of the elongated support members 202 are preferably positioned circumferentially about the annular engagement end 65 of the prosthetic "ribbon structure" valve 10b.

As additionally illustrated in FIG. 3B, the support structure base 210 is preferably disposed proximate the distal end 63 of prosthetic "ribbon structure" valve 10b. The elongated support members 202 are also operatively connected to and extend outwardly from the support structure base 210.

In a preferred embodiment, at least one elongated support member 202 extends outwardly along and is positioned substantially coincident with at least one elongated ribbon member 60. More preferably, each of the elongated support members 202 are positioned substantially coincident with each of the elongated ribbon members 60.

In some embodiments of the invention, at least one elongated support member 202 of the adaptive support structure 200 is operatively connected or engaged to a ribbon member 60.

According to the invention, the elongated support members 202 of the adaptive support structure 200 can be operatively connected to the ribbon members 60 by various conventional means, including, without limitation, sutures, biocompatible adhesive compositions, etc.

According to the invention, the adaptive support structure 200 can comprise a biocompatible metal or any of the aforementioned mammalian-based tissues (and compositions comprising same) and polymeric compositions.

In some embodiments, the adaptive support structure 200 comprises a shape-memory alloy.

In a preferred embodiment of the invention, the shape-memory alloy comprises a nickel-titanium alloy.

In some embodiments, the nickel-titanium alloy comprises Nitinol®.

In some embodiments of the invention, the adaptive support structure 200 is configured to transition from a pre-deployment configuration, wherein the prosthetic "ribbon structure" valve associated therewith can be positioned proximate a valve annulus, to an expanded post-deployment configuration.

In such embodiments, when the adaptive support structure 200 transitions to the expanded post-deployment configuration, the adaptive support structure 200 conforms to the annular engagement ends of prosthetic "ribbon structure" valves associated therewith, e.g., annular engagement end 65 of prosthetic "ribbon structure" valve 10b and, in some embodiments, a valve annulus when the annular engagement ends of the prosthetic "ribbon structure" valves is in contact therewith.

According to the invention, transition of the adaptive support structure 200 from a pre-deployment configuration to a post-deployment configuration can be achieved or induced by various conventional means.

In some embodiments of the invention, transition of the adaptive support structure 200 from a pre-deployment configuration to a post-deployment configuration is achieved or induced by applying a radial force to the adaptive support structure 200 and/or an interior region of the prosthetic "ribbon structure" valve associated therewith, such as by a conventional balloon catheter device.

In some embodiments of the invention, transition of the adaptive support structure 200 from a pre-deployment configuration to a post-deployment configuration is achieved or induced by virtue of the adaptive support structure 200 composition, i.e., the adaptive support structure 200 comprises a shape-memory alloy, such as Nitinol®.

As indicated above, in a preferred embodiment of the invention, the adaptive support structure 200 is designed, configured and adapted to exert at least one, more preferably, a plurality of retaining forces, on the annular engagement end 65 of prosthetic "ribbon structure" valve 10b (and, hence, prosthetic valves 10c, 10e, 10f and 10h, discussed below), whereby the support structure 200 (i) conforms to the annular engagement end 65 of prosthetic "ribbon structure" valve 10b (and, hence, prosthetic valves 10c, 10e, 10f and 10h), (ii) securely positions the annular engagement end 65 of the prosthetic valve 10b adjacent to and, thereby, in contact with a target valve annulus valve, whereby the annular engagement end 65 of prosthetic "ribbon structure" valve 10b conforms to the shape of the valve annulus, and (iii) the annular engagement end 65 of the prosthetic valve 10b and, thereby, prosthetic valve 10b adapt to at least one fluctuation in the configuration and/or dimension of the valve annulus, whereby the annular engagement end 65 of the prosthetic valve 10b maintains contact therewith.

In some embodiments of the invention, when the adaptive support structure 200 exerts the retaining force(s) on the annular engagement end 65 of prosthetic "ribbon structure" valve 10b (and, hence, prosthetic valves 10c, 10e, 10f and 10h), the adaptive support structure 200 is further adapted to maintain contact of the annular engagement end 65 of the prosthetic valve 10b to the valve annulus for a predetermined period of time.

As indicated above, in a preferred embodiment of the invention, the support structure 200 (and support structures 250 and 300, discussed herein) is further designed, configured and adapted to provide at least one outwardly directed retaining force to the annular engagement end 65 of prosthetic "ribbon structure" valve 10b and the annular engagement ends of the other prosthetic valves of the invention.

More preferably, the support structure 200 (and support structures 250 and 300, discussed herein) is designed, configured and adapted to provide at least one outwardly directed force proximate the proximal end 206a of at least one of the elongated support members 202 (and proximate the proximal end 306a of support members 302) and, thereby, the proximal end 64 of at least one ribbon member 60.

More preferably, the support structure 200 (and support structures 250 and 300) are designed, configured and adapted to provide a plurality of outwardly directed retaining forces proximate the proximal ends 206a of the elongated support members 202 (and proximate the proximal end 306a of support members 302) and, thereby the proximal ends 64 of the ribbon members 60.

In some embodiments of the invention, the retaining force or forces provided by support structure 200 (and support structures 250 and 300) are preferably in the range of 0.2-0.5 lbs.

In some embodiments, the proximal ends 206a of the support members 202 comprise anchored ends that are adapted to engage, cardiovascular tissue and, thereby, position and secure the elongated support members 202 and, hence, prosthetic "ribbon structure" valve 10a associated therewith to a valve annulus and maintain engagement thereto for an enhanced support time period.

According to the invention, the anchored ends can comprise any suitable anchoring mechanism that is configured to engaged cardiovascular tissue and, thereby, position and secure a support member of the invention and, hence, a prosthetic valve associated therewith to a valve annulus.

In some embodiments, the anchored ends comprise barbed ends. In some embodiments, the anchored ends comprise deployable barbed ends, where the barbs are configured to transition from a recessed pre-deployment position to an extended post-deployment configuration.

Figure 3C:
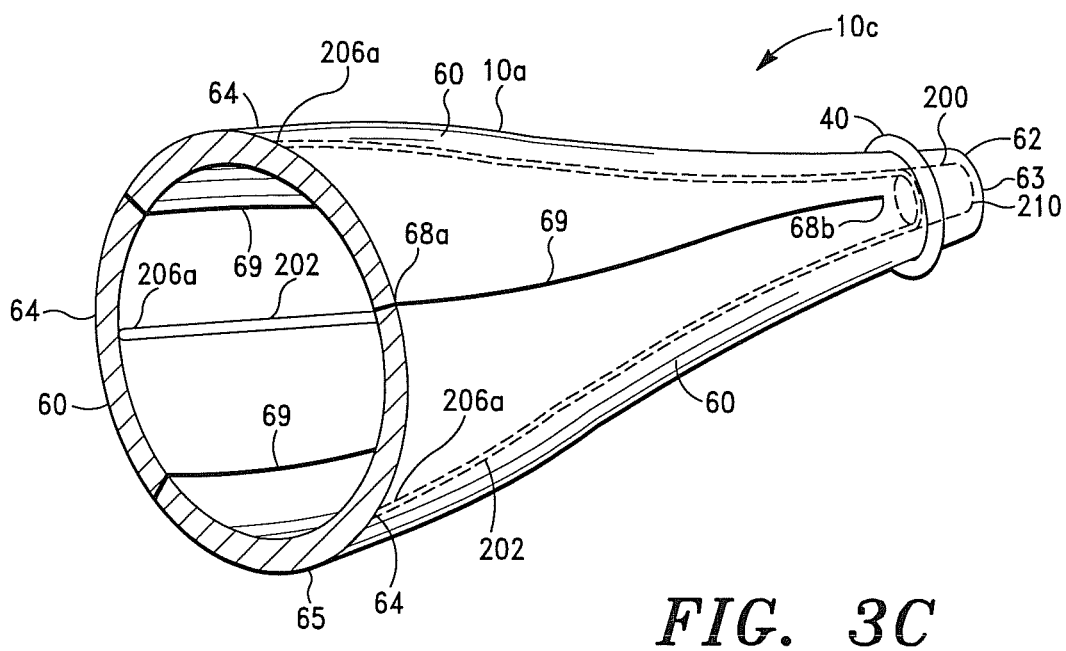
FIG. 3C is a perspective partial sectional view of another embodiment of the prosthetic "ribbon structure" valve shown in FIG. 3B having a structural ring disposed at the distal end of the valve, in accordance with the invention.

Referring now to FIG. 3C, there is shown another embodiment of the prosthetic "ribbon structure" valve 10b that is shown in FIG. 3B. As illustrated in FIG. 3C, the prosthetic "ribbon structure" valve, now denoted 10c, includes a structural ring 40 that is disposed on the distal end 63 of the prosthetic valve 10c.

According to the invention, the structural ring 40 can be disposed at any position on the closed distal valve region 63' of prosthetic "ribbon structure" valve 10c.

Figure 3D:
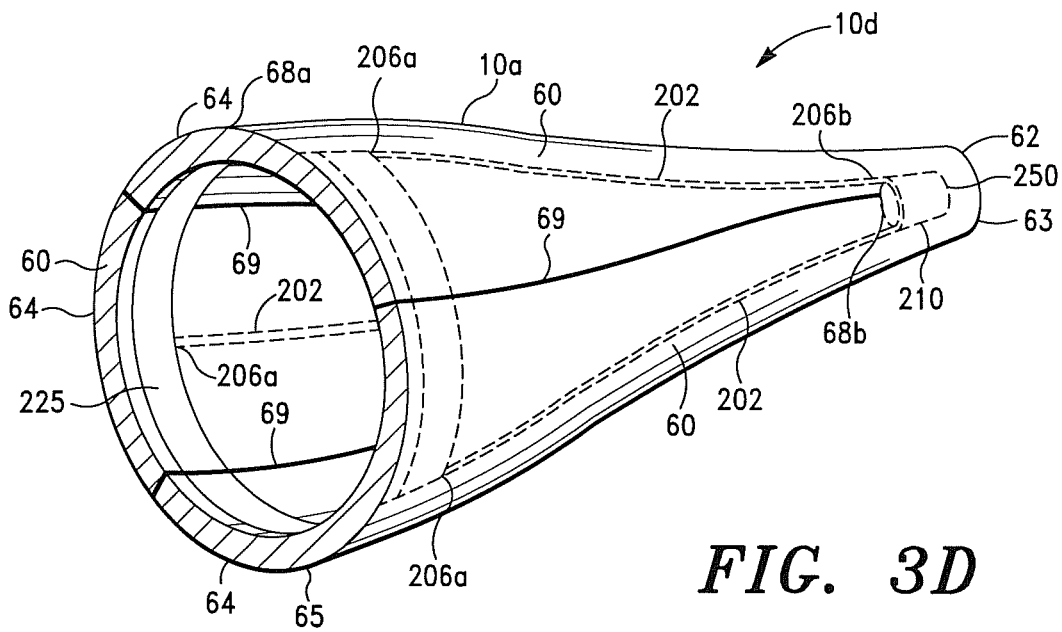
FIG. 3D is a perspective partial sectional view of another embodiment of the prosthetic "ribbon structure" valve shown in FIG. 3B having a further embodiment of an adaptive support structure associated therewith, in accordance with the invention.

Referring now to FIG. 3D, there is shown yet another embodiment of prosthetic "ribbon structure" valve 10b that is shown in FIG. 3B, wherein the prosthetic valve, now denoted 10d, includes another embodiment of an adaptive support structure of the invention, denoted 250.

Figure 3E:
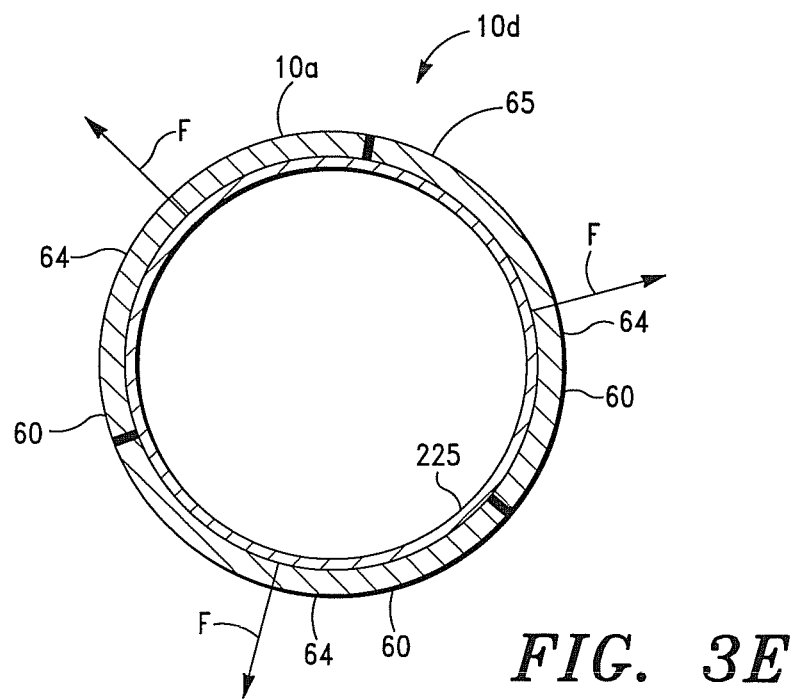
FIG. 3E is an end plane view of the annular engagement end of the prosthetic "ribbon structure" valve shown in FIG. 3D, in accordance with the invention.

As illustrated in FIGS. 3D and 3E, the adaptive support structure 250 includes an annular ring 225, which is positioned proximate the proximal ends 206a of the adaptive support structure 250 elongated support members 202 and, hence, as illustrated in FIG. 3D, proximate the annular engagement end 65 of prosthetic "ribbon structure" valve 10d.

According to the invention, the annular ring 225 can comprise an integral component or separate member.

In some embodiments of the invention, the annular ring 225 and, thereby, support structure 250, is similarly configured to transition from a pre-deployment configuration, wherein a prosthetic "ribbon structure" valve associated therewith can be positioned proximate a valve annulus, to an expanded post-deployment configuration.

In such embodiments, when the annular ring 225 and, thereby, support structure 250, transitions to the expanded post-deployment configuration, the annular ring 225 and, thereby, support structure 250, conforms to the annular engagement ends of the prosthetic "ribbon structure" valves associated therewith and, in some embodiments, a valve annulus when the annular engagement end of the prosthetic "ribbon structure" valves is in contact therewith.

According to the invention, transition of the annular ring 225 and, thereby, support structure 250, from a pre-deployment configuration to a post-deployment configuration can similarly be achieved or induced by various conventional means.

In some embodiments of the invention, transition of the annular ring 225 and, thereby, support structure 250, from a pre-deployment configuration to a post-deployment configuration is achieved by applying a radial force to the annular ring 225 and/or an interior region of the prosthetic "ribbon structure" valve associated therewith, such as by a conventional balloon catheter device.

In some embodiments of the invention, transition of the annular ring 225 and, thereby, support structure 250, from a pre-deployment configuration to a post-deployment configuration is achieved or induced by virtue of the adaptive support structure 250 composition, i.e., the annular ring 225 and/or adaptive support structure 250 comprises a shape-memory alloy, such as Nitinol®.

As indicated above, in a preferred embodiment of the invention, the annular ring 225 and, thereby, support structure 250, are similarly designed, configured and adapted to exert at least one, more preferably, a plurality of retaining forces, on the annular engagement end 65 of prosthetic "ribbon structure" valve 10d (and, hence, prosthetic valve 10g, discussed below), as shown in FIG. 3E, whereby the annular ring 225 and, thereby, support structure 250 similarly (i) conform to the annular engagement end 65 of prosthetic "ribbon structure" valve 10d (and, hence, prosthetic valve 10g), (ii) securely position the annular engagement end 65 of the prosthetic "ribbon structure" valve 10d adjacent to and, thereby, in contact with a target valve annulus valve, whereby the annular engagement end 65 of prosthetic "ribbon structure" valve 10d and, thereby, prosthetic "ribbon structure" valve 10d conforms to the shape of the valve annulus, and (iii) the annular engagement end 65 of the prosthetic "ribbon structure" valve 10d adapts to at least one fluctuation in the configuration and/or dimension of the valve annulus, whereby the annular engagement end 65 of the prosthetic "ribbon structure" valve 10d maintains contact therewith.

In some embodiments of the invention, when the adaptive support structure 250 exerts the retaining force(s) on the annular engagement end 65 of prosthetic "ribbon structure" valve 10d (and, hence, prosthetic valve 10g), the adaptive support structure 250 is further adapted to maintain contact of the annular engagement end 65 of the prosthetic "ribbon structure" valve 10d to the valve annulus for a predetermined period of time.

As indicated above, in some embodiments of the invention, the annular ring 225 comprises a microneedle anchoring mechanism that is further configured and adapted to engage the annular engagement end 65 of prosthetic "ribbon structure" valve 10d, engage cardiovascular tissue of the valve annulus and, thereby, position the prosthetic valve 10d proximate the valve annulus.

According to the invention, the prosthetic "ribbon structure" valve 10b (and, hence, prosthetic valves 10c, 10d, 10f, 10g, 10h and 10i) can further comprise at least one supplemental support structure, such as described in Applicant's U.S. Pat. Nos. 10,188,509, 10,188,510 and 10,052,409, which are also incorporated by reference herein.

Figure 3F:
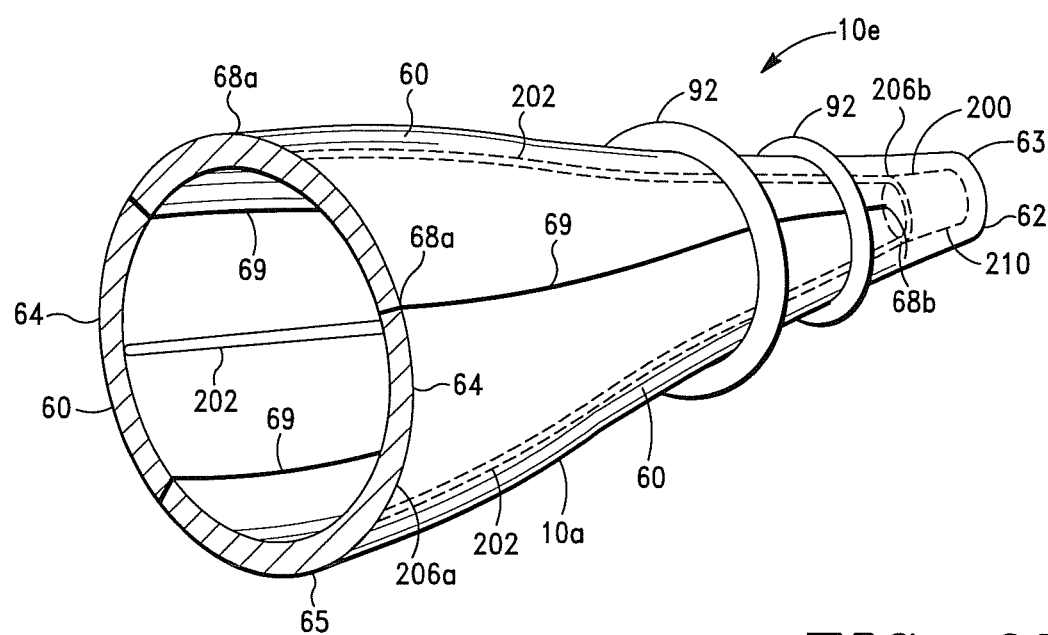
FIG. 3F is a perspective partial sectional view of another embodiment of the prosthetic "ribbon structure" valve shown in FIG. 3B having supplemental support structures disposed between the annular engagement end and distal end of the valve, in accordance with the invention.

Referring now to FIG. 3F, there is shown an embodiment of prosthetic "ribbon structure" valve 10b that is shown in FIG. 3B, wherein the prosthetic "ribbon structure" valve, now denoted 10e, includes multiple supplemental support structures (denoted "92") that are disposed proximate the mid-region of prosthetic "ribbon structure" valve 10e to enhance the structural integrity of the prosthetic valve 10e.

According to the invention, the supplemental support structures 92 can be disposed at any point on a prosthetic valve of the invention.

Figure 3G:
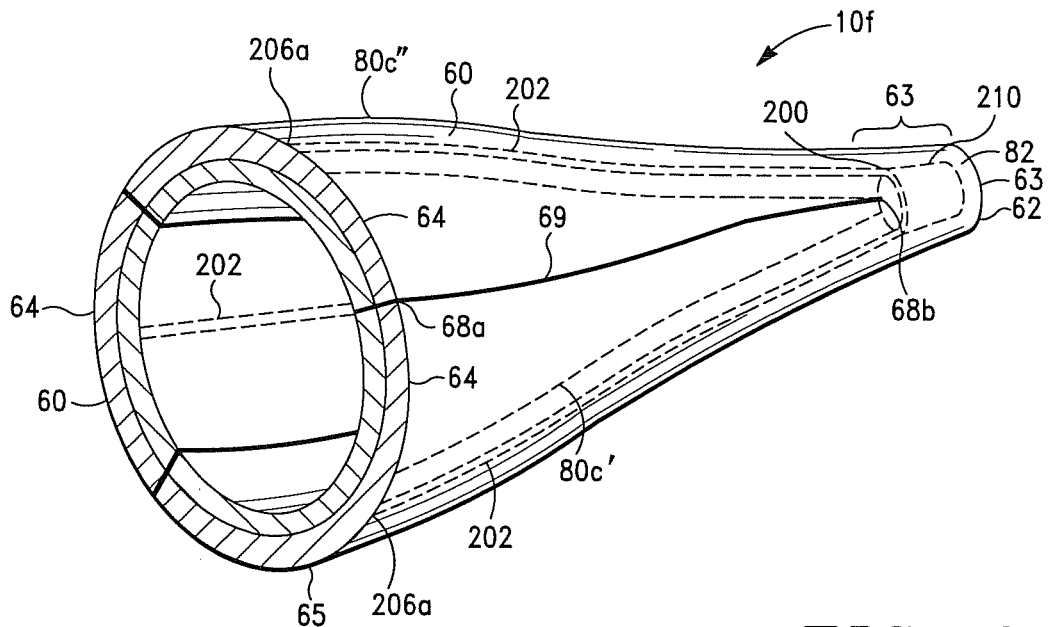
FIG. 3G is a perspective partial sectional view of another embodiment of the prosthetic "ribbon structure" valve shown in FIG. 3B formed from multiple overlaid base "ribbon structure" valve members, i.e., a multi-sheet prosthetic "ribbon structure" valve having one embodiment of an adaptive support structure associated therewith, in accordance with the invention.

Referring now to FIG. 3G, there is shown another embodiment of prosthetic "ribbon structure" valve 10a that is shown in FIG. 3B, wherein the prosthetic valve, now denoted 10f, is formed from and, hence, comprises two (2) seamless pre-formed sheet structures or members, 80c', 80c" i.e., a multi-sheet base "ribbon structure" valve member.

According to the invention, in some embodiments of the invention, the inner and outer sheet members 80c', 80c" can comprise sheet member 80a shown in FIG. 2A, wherein prosthetic "ribbon structure" valve 10f is formed by positioning the adaptive support member 200 between the inner 80c' and outer 80c" sheet members.

In some embodiments of the invention, the inner sheet member 80c' comprises sheet member 80a shown in FIG.

2A and the outer sheet member 80c″ comprises sheet member 80b shown in FIG. 3A, such as illustrated in FIG. 3G, wherein, when sheet members 80c′, 80c″ are folded inwardly and form prosthetic "ribbon structure" valve 10f, support member 200 is similarly positioned between the inner 80c′ and outer 80c″ sheet members.

According to the invention, the support structure 200 can also be disposed proximate the inner surface of the inner sheet member 80c′.

Figure 3H:
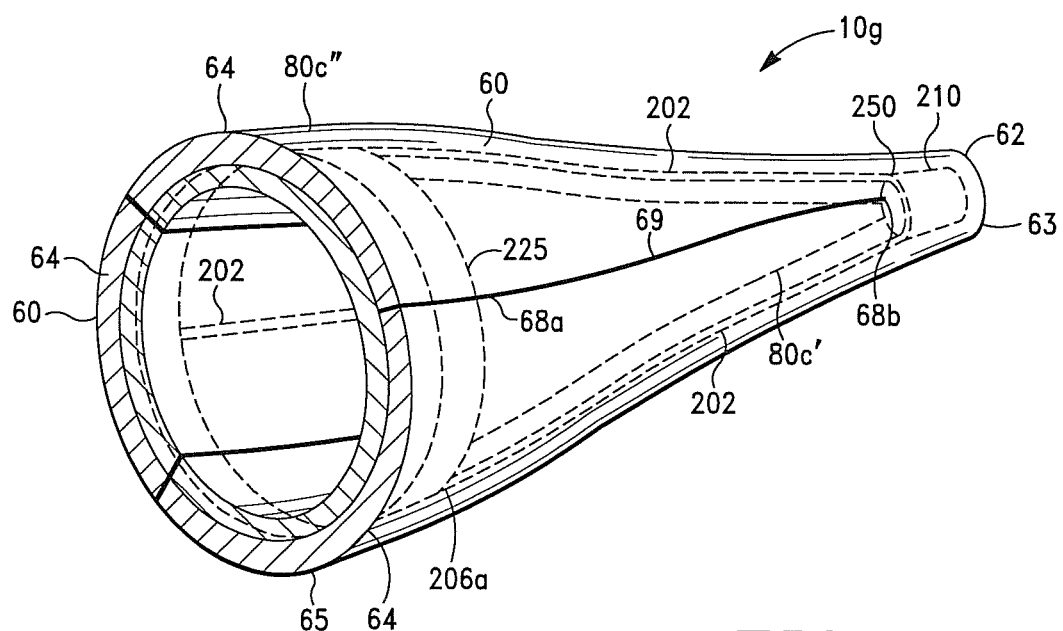
FIG. 3H is a perspective partial sectional view of another embodiment of the multi-sheet prosthetic "ribbon structure" valve shown in FIG. 3G having a further embodiment of an adaptive support structure associated therewith, in accordance with the invention.

Referring now to FIG. 3H, there is shown another embodiment of prosthetic "ribbon structure" valve 10f that is shown in FIG. 3G, wherein the prosthetic valve, now denoted 10g, comprises support structure 250, and the annular ring 225 of the support structure 250 is disposed on the annular engagement end 65 of the prosthetic valve 10g.

As illustrated in FIG. 3H, in a preferred embodiment, the support structure 250 and, hence, annular ring 225 is similarly disposed between inner and outer sheet structures or members 80c′ and 80c″ of prosthetic "ribbon structure" valve 10g.

However, as indicated above, according to the invention, the support structure 250 can similarly be disposed proximate the inner surface of the inner sheet structure 80c′ of prosthetic "ribbon structure" valve 10g.

According to the invention, the prosthetic "ribbon structure" valve 10b (and, hence, prosthetic valves 10c, 10d, 10e, 10f, 10g, 10h) can further comprise a stent structure, such as described in Applicant's U.S. Pat. No. 10,188,513, which is incorporated by reference herein in its entirety.

Figure 4A:
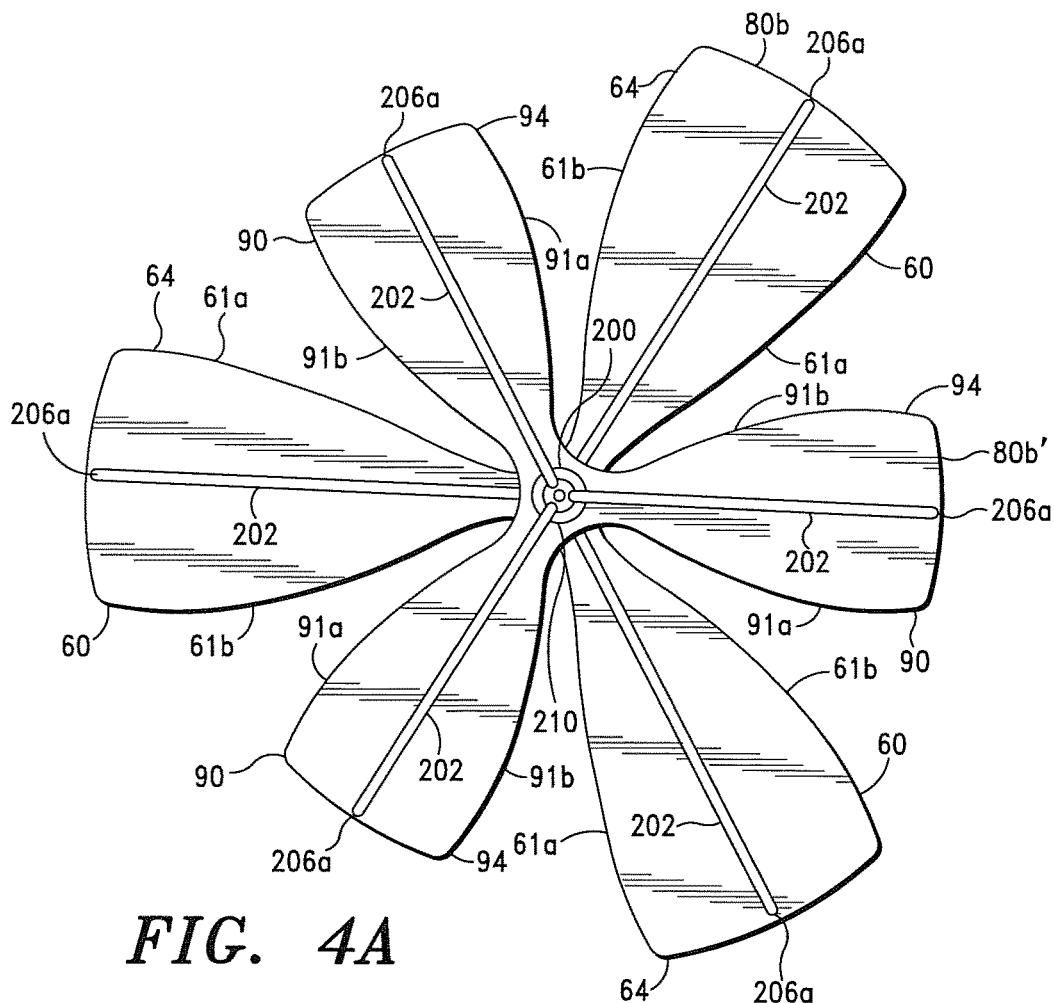
FIG. 4A is a top plan view of one embodiment of a multi-sheet base "ribbon structure" member having one embodiment of an adaptive support structure associated therewith in a pre-formed configuration, in accordance with the invention.
Figure 4B:
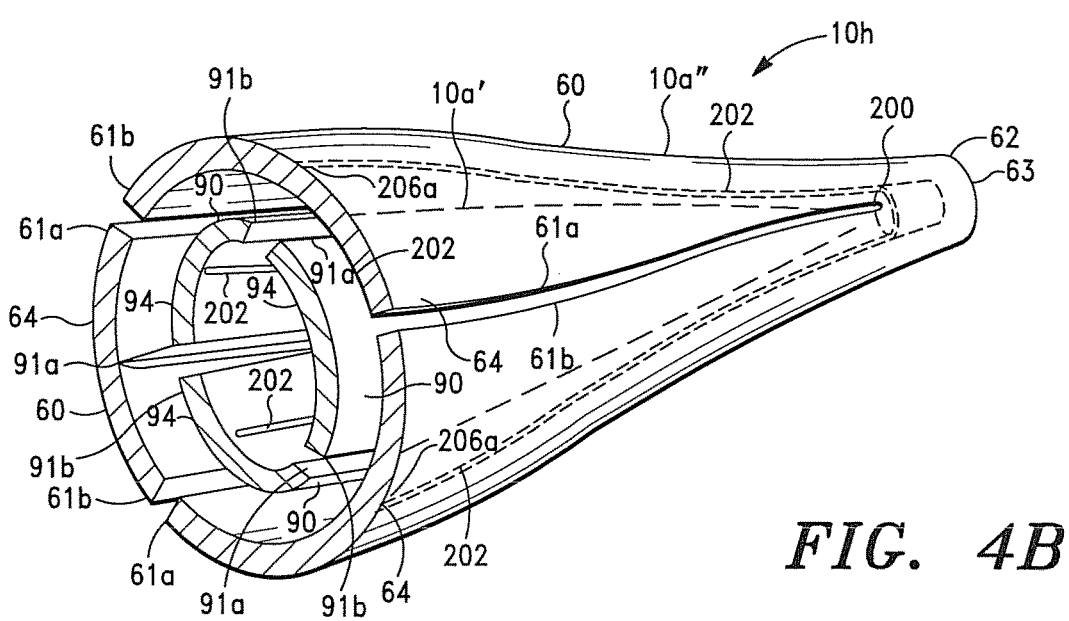
FIG. 4B is a perspective view of the multi-sheet base "ribbon structure" valve member shown in FIG. 4A in a formed operational configuration, i.e., a formed prosthetic "ribbon structure" valve having the adaptive support structure shown in FIG. 4A associated therewith, in accordance with the invention, in accordance with the invention.

Referring now to FIGS. 4A and 4B, a further embodiment of a prosthetic "ribbon structure" valve of the invention having a multi-sheet base valve member will be described in detail.

As illustrated in FIG. 4B, the prosthetic "ribbon structure" valve, denoted 10h, comprises a first base valve member, denoted 10a′, and second base valve member, denoted 10a″, which, according to the invention, are similar to (and, hence, function similarly to) sheet member 10a shown in FIG. 2A. However, in the illustrated embodiment, the first or outer base valve member 10a′ is formed from sheet member 80b shown in FIG. 3A (or a similar sheet member) and the second or inner base valve member 10a″ is formed from sheet member 80b′ shown in FIG. 4A.

As illustrated in FIG. 4A, the ribbon members 90 of the second or inner base valve member 10a″ are preferably shorter in length than the ribbon members 60 of the first or outer base valve member 10a′.

As further illustrated in FIG. 4A, except for the length, sheet member 80b′ is similar to sheet member 80b, having adaptive support structure 200 positioned thereon.

According to the invention, the ribbon members 60 and 90 can similarly comprise various widths proximate the proximal ends 64 and 94 of ribbon members 60 and 90.

Figure 5A:
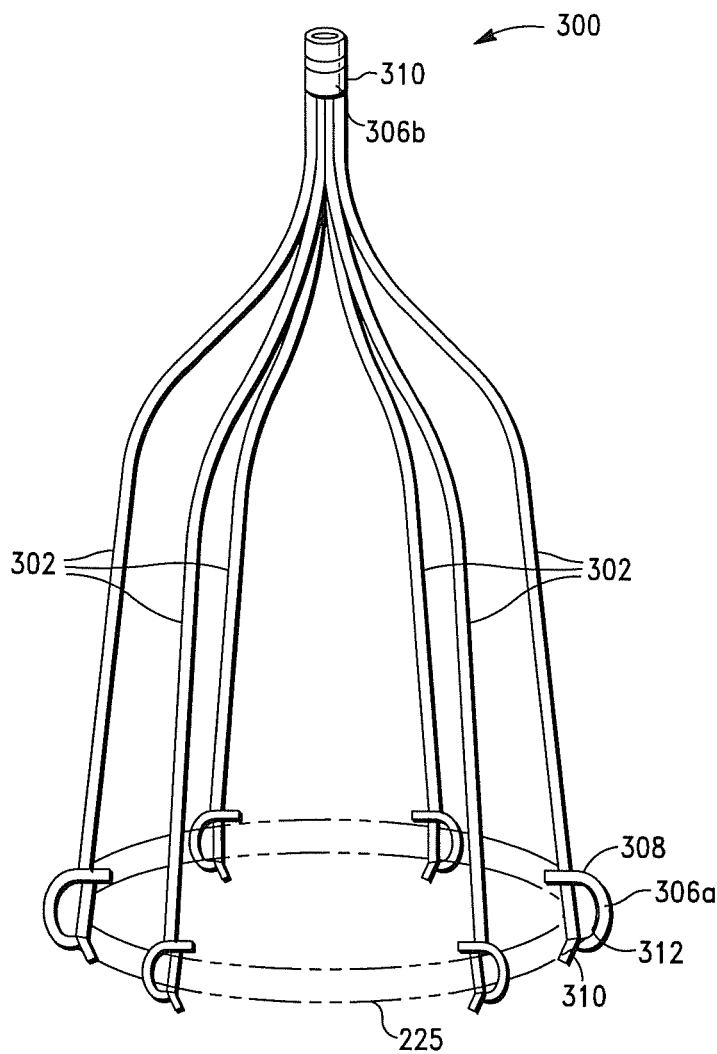
FIG. 5A is perspective view of another embodiment of an adaptive support structure, in accordance with the invention.
Figure 5B:
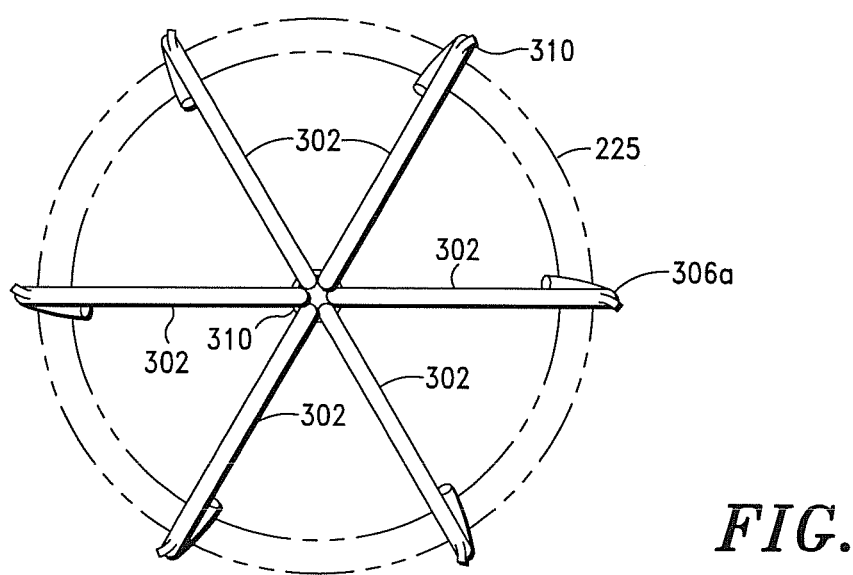
FIG. 5B is an end plane view of the adaptive support structure shown in FIG. 5A, in accordance with the invention.

Referring now to FIGS. 5A and 5B, there is shown another embodiment of an adaptive support structure of the invention, denoted 300. As illustrated in FIGS. 5A and 5B, in a preferred embodiment, the adaptive support structure 300 comprises a base structure 310 and a plurality of elongated support members 302 having proximal and distal ends 306a, 306b.

According to the invention, the support structure 300 can similarly comprise any of the aforementioned biocompatible metals, mammalian-based tissues and compositions formed therewith, and polymeric compositions.

In some embodiments of the invention, the adaptive support structure 300 is similarly configured to transition from a pre-deployment configuration, wherein a prosthetic "ribbon structure" valve associated therewith can be positioned proximate a valve annulus, to an expanded post-deployment configuration.

In such embodiments, when the adaptive support structure 300 transitions to the expanded post-deployment configuration, the adaptive support structure 300 will similarly conform to the annular engagement end of the prosthetic "ribbon structure" valves associated therewith, and, in some embodiments, a valve annulus when the annular engagement end of the prosthetic "ribbon structure" valves is in contact therewith.

According to the invention, transition of the adaptive support structure 300 from a pre-deployment configuration to a post-deployment configuration can similarly be achieved or induced by various conventional means.

Thus, in some embodiments of the invention, transition of the adaptive support structure 300 from a pre-deployment configuration to a post-deployment configuration is similarly achieved by applying a radial force to the adaptive support structure 300 and/or an interior region of the prosthetic "ribbon structure" valve associated therewith, such as by a conventional balloon catheter device.

In some embodiments of the invention, transition of the adaptive support structure 300 from a pre-deployment configuration to a post-deployment configuration is similarly achieved or induced by virtue of the adaptive support structure 300 composition, i.e., the adaptive support structure 200 comprises a shape-memory alloy, such as Nitinol®.

In a preferred embodiment, the adaptive support structure 300 is similarly designed, configured and adapted to exert at least one, more preferably, a plurality of retaining forces on the annular engagement ends of the prosthetic "ribbon structure" valves of the invention, whereby the adaptive support structure 300 similarly (i) conforms to the annular engagement ends of the prosthetic "ribbon structure" valves, (ii) securely positions the annular engagement ends of the prosthetic "ribbon structure" valves adjacent to and, thereby, in contact with a target valve annulus valve, whereby the annular engagement ends of the prosthetic "ribbon structure" valves conform to the shape of the valve annulus, and (iii) the annular engagement ends of the prosthetic "ribbon structure" valves and, thereby, the prosthetic "ribbon structure" valves adapt to at least one fluctuation in the configuration and/or dimension of the valve annulus, whereby the annular engagement ends of the prosthetic "ribbon structure" valves maintain contact therewith.

In some embodiments of the invention, when the adaptive support structure 300 exerts the retaining force on the annular engagement ends of the prosthetic "ribbon structure" valves, the adaptive support structure 300 is further adapted to maintain contact of the annular engagement ends of the prosthetic "ribbon structure" valves to the valve annulus for a predetermined period of time.

According to the invention, the elongated support members 302 of the adaptive support structure 300 can similarly comprise any length and shape. In some embodiments, the elongated support members 302 comprise a length in the range of 20-200 mm, more preferably, a length in the range of 35-45 mm.

In some embodiments, the elongated support members 302 comprise alternating lengths in the range of 20-200 mm, more preferably, a length in the range of 35-45 mm. By way of example, an adaptive support structure comprising six (6) elongated support members can comprise three (3) elongated support members with a length of 38 mm and three (3)

elongated support members with a length of 40 mm, where the elongated support members are arranged according to alternating length.

In a preferred embodiment, elongated support members 302 are also flexible.

In some embodiments, the elongated support members 302 are deformable.

Figure 5C:
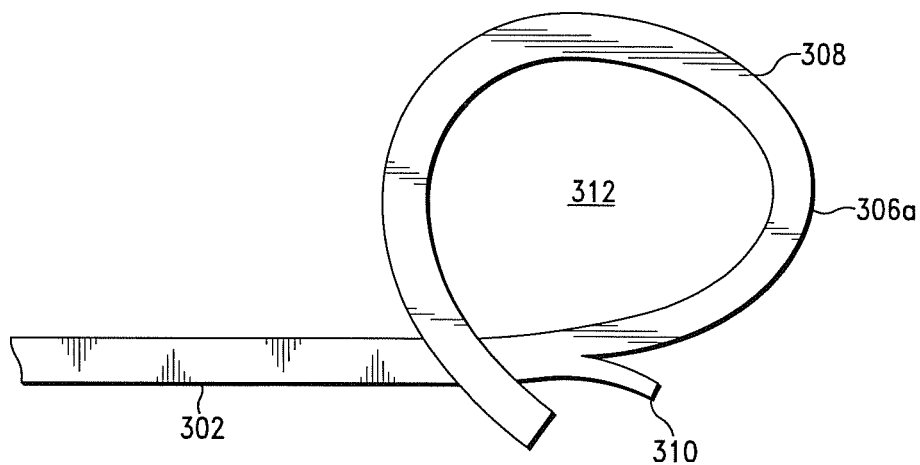
FIG. 5C is a side plan view of one embodiment of a proximal end of an adaptive support structure member, in accordance with the invention.

As illustrated in FIGS. 5A and 5C, in a preferred embodiment, the proximal ends 306a of the elongated support members 302 comprise looped structures 308 comprising anchored tips 310 and circumferential regions 312.

As illustrated in FIGS. 5A and 5B, the circumferential regions 312 of the elongated support members 302 can be configured to receive annular ring 225 (and, hence, annular ring 400, discussed below), which is shown in phantom, and secure the annular ring 225 to the adaptive support structure 300.

Figure 5D:
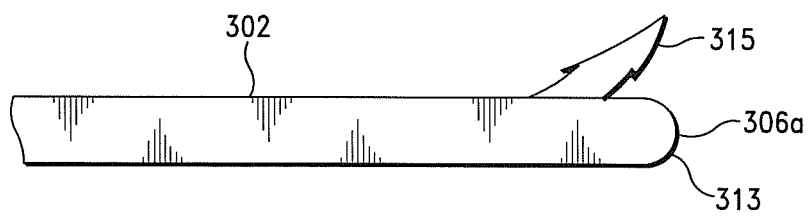
FIG. 5D is a side plan view of another embodiment of a proximal end of an adaptive support structure member, in accordance with the invention.

Referring now to FIG. 5D, there is shown another embodiment of distal ends 306a of elongated support members 302. As illustrated in FIG. 5D, the distal ends 306a comprise an anchored distal end 313 having a deployable anchoring member 315.

In some embodiments, the anchored end 313 is configured to transition from a recessed pre-deployment position to an extended post-deployment configuration, wherein the anchoring member 315 is deployed in an extended position.

According to the invention, the deployable anchoring member 315 can comprise any suitable anchoring mechanism that is configured to deploy an anchoring member that is adapted to engage tissue of a cardiovascular structure; particularly, a valve annulus, position a support structure and, hence, prosthetic valve of the invention associated therewith, proximate the cardiovascular structure, and maintain contact of the prosthetic valve to the cardiovascular structure.

According to the invention, the adaptive support structure 300 can comprise various configurations. Referring now to FIGS. 6A-6E, there are shown five (5) alternative shapes and configurations and, hence, additional embodiments of the adaptive support structure 300 shown in FIG. 5A.

Figure 7A:
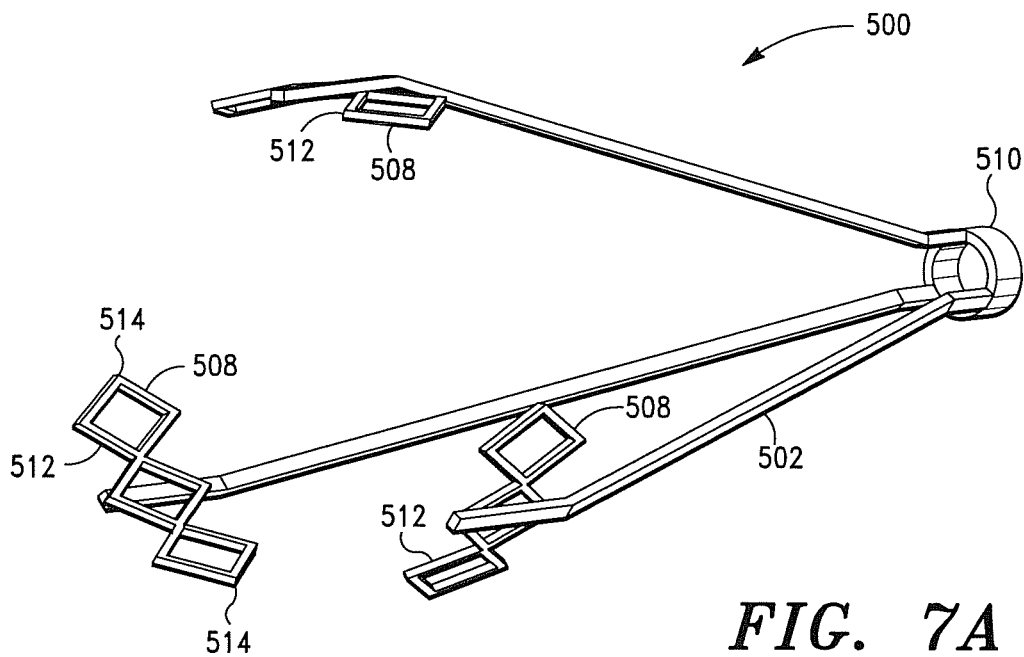
FIG. 7A is a perspective view of a further embodiment of an adaptive support structure, in accordance with the invention.

Referring now to FIG. 7A, there is shown another embodiment of an adaptive support structure 500 of the invention.

As illustrated in FIG. 7A, adaptive support structure 500 comprises a multi-link support structure that comprises discontinuous, cross-linked circumferential proximal end regions 508, a cylindrical distal end region 510, and a plurality of elongated support members 502 that are positioned and configured to connect the cross-linked circumferential proximal end regions 508 to the cylindrical distal end region 510.

In a preferred embodiment, the elongated support members 502 comprise flexible members. In some embodiments, the elongated support members 502 are deformable.

According to the invention, the adaptive support structure 500 can similarly comprise any of the aforementioned biocompatible metals, mammalian-based tissues (and compositions comprising same, e.g., an ECM composition), and polymeric compositions.

In some embodiments, the adaptive support structure 500 similarly comprises a nickel-titanium alloy, such as Nitinol®.

Figure 7B:
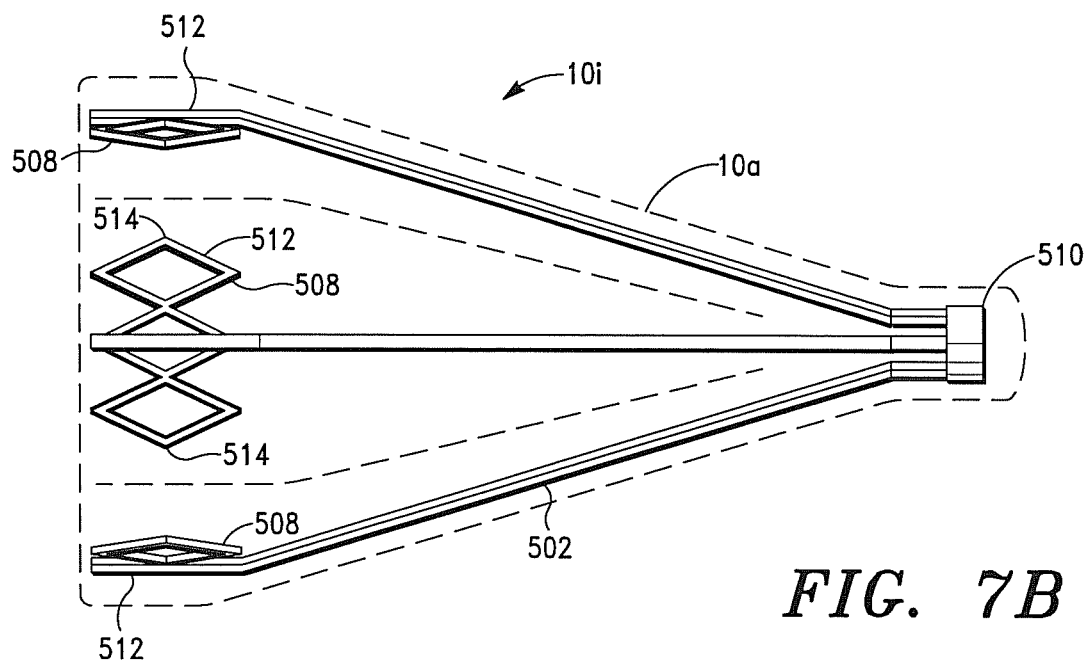
FIG. 7B is a side plan view of one embodiment of a prosthetic "ribbon structure" valve employing the adaptive support structure shown in FIG. 7A, in accordance with the invention.

In a preferred embodiment, the adaptive support structure 500 is similarly configured to transition from a pre-deployment configuration, wherein the ends 514 of the discontinuous, cross-linked circumferential proximal end regions 508 are in communication with each other and a prosthetic "ribbon structure" valve associated therewith can be disposed in a valve annulus, to a post-deployment configuration, such as shown in FIG. 7B, wherein the prosthetic "ribbon structure" valve associated therewith can be positioned proximate a valve annulus, to an expanded post-deployment configuration.

In some embodiments, the cross-linked circumferential proximal end regions 508 of the adaptive support structure 500 comprise magnetized ends 514 that are configured to self-align and maintain communication with each other when the adaptive support structure 500 (and, hence, prosthetic "ribbon structure" valve associated therewith) is in a pre-deployment configuration.

According to the invention, transition of the adaptive support structure 500 from a pre-deployment configuration to a post-deployment configuration can similarly be achieved or induced by various conventional means.

Thus, in some embodiments of the invention, transition of the adaptive support structure 500 from a pre-deployment configuration to a post-deployment configuration is similarly achieved by applying a radial force to the adaptive support structure 500 and/or an interior region of the prosthetic "ribbon structure" valve associated therewith, such as by a conventional balloon catheter device.

In some embodiments of the invention, transition of the adaptive support structure 500 from a pre-deployment configuration to a post-deployment configuration is similarly achieved or induced by virtue of the adaptive support structure 500 composition, i.e., the adaptive support structure 500 comprises a shape-memory alloy, such as Nitinol®.

In a preferred embodiment, the adaptive support structure 500 is similarly designed, configured and adapted to exert at least one, more preferably, a plurality of retaining forces on the annular engagement ends of the prosthetic "ribbon structure" valves of the invention, whereby the support structure 500 similarly (i) conforms to the annular engagement end of prosthetic "ribbon structure" valves, (ii) securely positions the annular engagement ends of the prosthetic "ribbon structure" valves adjacent to and, thereby, in contact with a target valve annulus valve, whereby the annular engagement ends of the prosthetic "ribbon structure" valves conform to the shape of the valve annulus, and (iii) the annular engagement ends of the prosthetic "ribbon structure" valves and, thereby, the prosthetic "ribbon structure" valves adapt to at least one fluctuation in the configuration and/or dimension of the valve annulus, whereby the annular engagement ends of the prosthetic "ribbon structure" valves maintain contact therewith.

In some embodiments of the invention, when the adaptive support structure 500 exerts retaining force(s) on the annular engagement ends of the prosthetic "ribbon structure" valves, the adaptive support structure 500 is further adapted to maintain contact of the annular engagement ends of the prosthetic "ribbon structure" valves to the valve annulus for a predetermined period of time.

Referring now to FIG. 7B, there is shown one embodiment of prosthetic "ribbon structure" valve, denoted 10i, wherein the prosthetic "ribbon structure" valve 10i comprises base valve member 10a and the adaptive support structure 500 shown in FIG. 7A.

Figure 8A:
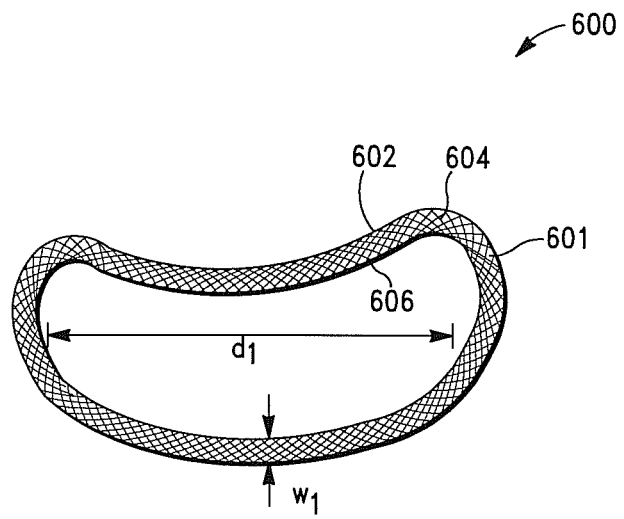
FIG. 8A is a perspective view of one embodiment of an expandable annular ring support member in a pre-deployment configuration, in accordance with the invention.
Figure 8B:
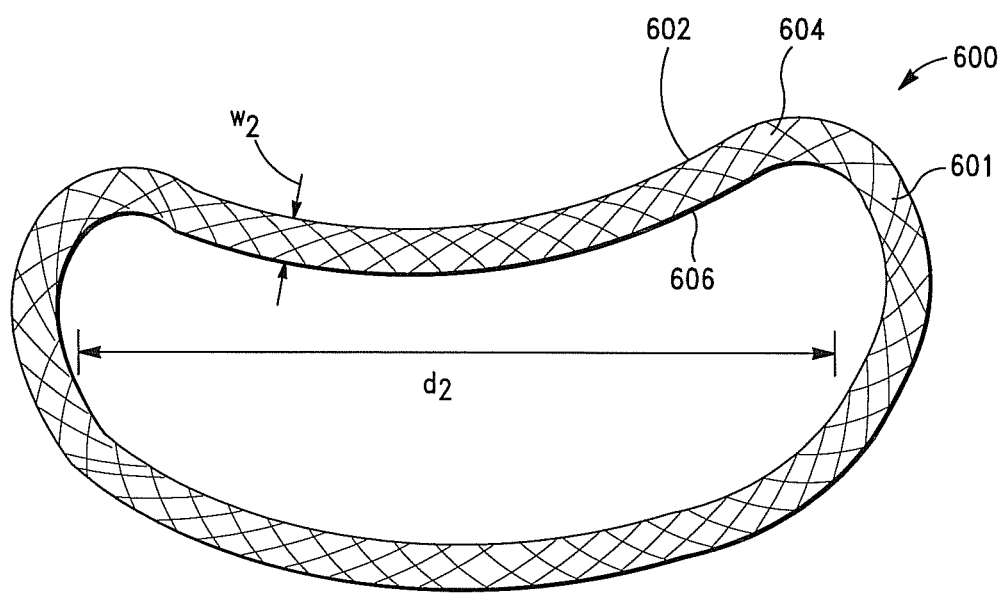
FIG. 8B is a perspective view of the expandable annular ring support member shown in FIG. 8A in an expanded post-deployment configuration, in accordance with the invention.

Referring now to FIGS. 8A and 8B, there is shown a further embodiment of a support structure of the invention, denoted 600.

As illustrated in FIGS. 8A and 8B, the support structure 600 comprises an expandable annular ring member 602.

According to the invention, the expandable annular ring member 602 can be employed in or with adaptive support structures 200 and 250, i.e., a component thereof, or as a separate support structure.

As illustrated in FIGS. 8A and 8B, in one embodiment, the annular ring member 602 preferably comprises at least one helically arranged fiber or cord element 601. In a preferred embodiment, the annular ring member 602 comprises a plurality of helically arranged fiber or cord elements 601, which form an expandable tubular ring configuration having a plurality of uniformly shaped closed, interconnecting cells 604.

According to the invention, the fiber elements 601, and, hence, annular ring member 602 formed therefrom, can comprise any of the aforementioned biocompatible metals, mammalian-based tissues (and compositions comprising same), and polymeric compositions.

In some embodiments, the fiber elements 601 comprise a nickel-titanium alloy, such as Nitinol®.

In some embodiments of the invention, the fiber elements 601 comprise Dyneema®, a high molecular weight polyethylene (HMPE).

As further illustrated in FIGS. 8A and 8B, in a preferred embodiment, the annular ring member 602 and, hence, expandable annular ring 600 is configured and adapted to transition from a pre-deployment configuration, wherein, as illustrated in FIG. 8A, the annular ring comprises a width $w_1$ and a diameter $d_1$, to a post-deployment configuration, wherein, as illustrated in FIG. 8B, the annular ring comprises a greater width $w_2$ and a greater diameter $d_2$, whereby, when the expandable annular ring 600 is disposed proximate an annular engagement end of a prosthetic "ribbon structure" valve of the invention, such as prosthetic "ribbon structure" valve 10a, the expandable annular ring 600 conforms to the annular engagement end of the prosthetic "ribbon structure" valve.

In a preferred embodiment, the expandable annular ring 600, when in the post-deployment configuration, is further similarly adapted to exert a retaining force on the annular engagement ends of the prosthetic "ribbon structure" valves of the invention, whereby the expandable annular ring 600 similarly (i) positions the annular engagement ends of the prosthetic "ribbon structure" valves adjacent to and, thereby, in contact with a target valve annulus, (ii) the annular engagements ends of the prosthetic "ribbon structure" valves conform to the shape of the valve annulus, and (iii) the annular engagement ends of the prosthetic "ribbon structure" valves and, thereby, the prosthetic "ribbon structure" valves adapt to at least one fluctuation in the configuration and/or dimension of the valve annulus, whereby the annular engagement ends of the prosthetic "ribbon structure" valves maintain contact therewith.

In some embodiments of the invention, when the expandable annular ring 600 exerts retaining force(s) on the annular engagement ends of the prosthetic "ribbon structure" valves, the expandable annular ring 600 is further adapted to maintain contact of the annular engagement ends of the prosthetic "ribbon structure" valves to the valve annulus for a predetermined period of time.

According to the invention, transition of the expandable annular ring 600 from a pre-deployment configuration to a post-deployment configuration can be achieved by various means.

In some embodiments of the invention, transition of the expandable annular ring 600 from a pre-deployment configuration to a post-deployment configuration is achieved by applying a radial force to the interior portion 606 of an expandable annular ring 602, such as by a conventional balloon catheter device.

In some embodiments of the invention, transition of the expandable annular ring 600 from a pre-deployment configuration to a post-deployment configuration is achieved or induced by virtue of the expandable annular ring 602 composition, i.e., the expandable annular ring 602 comprising a shape-memory alloy, such as Nitinol®.

In some embodiments of the invention, transition of the expandable annular ring 600 from a pre-deployment configuration to a post-deployment configuration is achieved or induced by a radial force provided and exerted to the interior portion 606 of the expandable annular ring 600 by the elongated support members of the adaptive support structures of the invention.

In some embodiments of the invention, the transition of the expandable annular ring 600 and, thereby, adaptive support structure 250, from a pre-deployment configuration to an expanded post-deployment configuration is achieved or induced by virtue of the configuration size of the annular ring 225, e.g., an overlapping expandable band configuration.

Figure 9A:
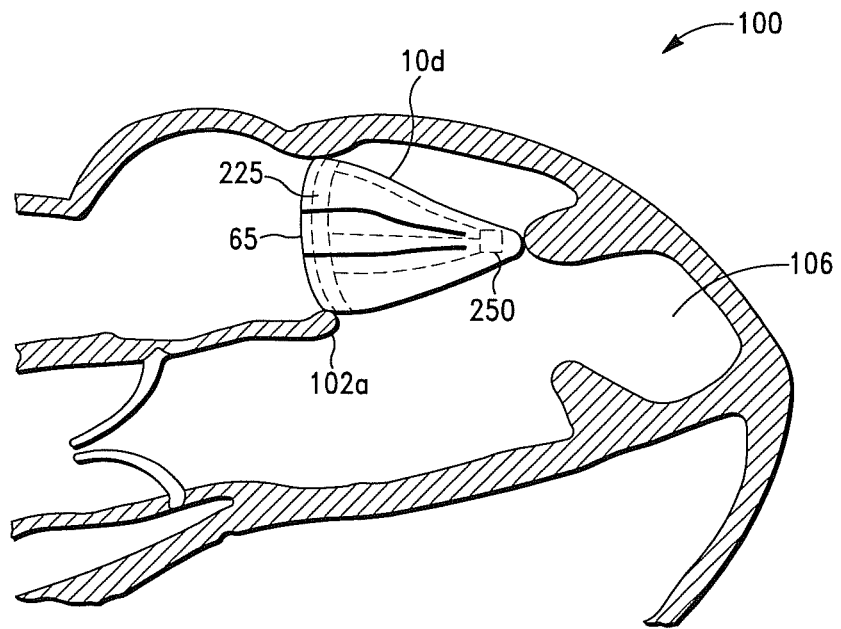
FIG. 9A is an illustration of the prosthetic valve shown in FIG. 3B secured to an expanded (or abnormally large) mitral valve annulus region, in accordance with the invention.

Referring now to FIG. 9A, there is shown prosthetic "ribbon structure" valve 10d disposed in an abnormally expanded mitral valve annulus region 102a of a subject.

As illustrated in FIG. 9A and discussed in detail above, the support structure 250 and, hence, annular engagement end 65 of prosthetic "ribbon structure" valve 10d is configured to (i) conform to the configuration and dimension of the abnormally expanded mitral valve annulus region 102a and (ii) adapt to at least one fluctuation in the configuration and/or dimension of the valve annulus 102a, whereby the annular engagement end 65 of prosthetic "ribbon structure" valve 10d maintains contact with (and maintains an effective seal with) the valve annulus 102a.

Figure 9B:
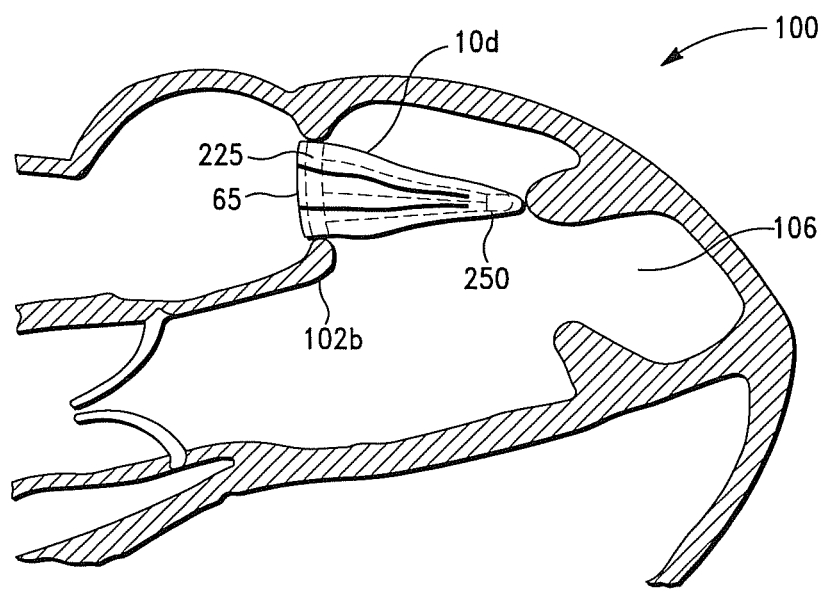
FIG. 9B is an illustration of the prosthetic valve shown in FIG. 3B secured to a normal mitral valve annulus region, in accordance with the invention.

As illustrated in FIG. 9B, the support structure 250 and, hence, annular engagement end 65 of prosthetic "ribbon structure" valve 10d is further adapted to (i) allow the expanded mitral valve annulus region 102a to return to a physiologically healthy valve annulus region state and, hence, size (denoted 102b), and (ii) maintain contact of the annular engagement end 65 of prosthetic "ribbon structure" valve 10d to the annulus region 102b.

According to the invention, the prosthetic "ribbon structure" valves and associated adaptive support structures of the invention can be delivered to or implanted in a subject using any conventional procedure.

In a preferred embodiment of the invention, the prosthetic "ribbon structure" valves and associated adaptive support structures of the invention are delivered to or implanted in a subject using a percutaneous implantation procedure.

In some embodiments, the prosthetic "ribbon structure" valves and associated adaptive support structures of the invention are delivered to or implanted in a subject using at least one system or method of implantation disclosed in Applicant's U.S. application Ser. No. 16/553,570, which is incorporated by reference herein in its entirety.

According to the invention, the prosthetic "ribbon structure" valves and associated adaptive support structures of the invention can be configured to have any suitable pre-deployment size and configuration. In some embodiments, the prosthetic "ribbon structure" valves and associated adaptive support structures of the invention are configured to compress down to a pre-deployment size of at least 6 French (a circumference of at least 6.28 mm).

As will readily be appreciated by one having ordinary skill in the art, the present invention provides numerous advantages compared to prior art prosthetic valves. Among the advantages are the following:

- The provision of prosthetic valves having an adaptable or dynamic annular engagement end or region adapted to engage a valve annulus, which will accommodate a broad range of valve annulus configurations and dimensions, and adapt to at least one fluctuation in the configuration and/or dimension of the valve annulus in vivo, whereby, the annular engagement end or region of the valves maintains sealed engagement to the valve annulus;
- The provision of prosthetic valves having means for secure, reliable, and consistent highly effective attachment to cardiovascular structures and/or tissue;
- The provision of prosthetic valves that significantly decrease or effectively eliminate the incidence of perivalvular leaks after implant in a subject;
- The provision of improved methods for attaching prosthetic valves to cardiovascular structures and/or tissue that significantly decrease or effectively eliminate the incidence of perivalvular leaks;
- The provision of improved prosthetic valves and methods for attaching same to cardiovascular structures and/or tissue that maintain or enhance the structural integrity of the valve when subjected to cardiac cycle induced forces;
- The provision of improved prosthetic valves and methods for attaching same to cardiovascular structures and/or tissue that preserve the structural integrity of the cardiovascular structure(s) when attached thereto;
- The provision of prosthetic valves that induce modulated healing, including host tissue proliferation, bioremodeling and regeneration of new tissue and tissue structures with site-specific structural and functional properties;
- The provision of prosthetic valves that induce adaptive regeneration in vivo;
- The provision of prosthetic valves that are capable of administering a pharmacological agent to host tissue and, thereby produce a desired biological and/or therapeutic effect;
- The provision prosthetic valves that can be implanted without removal of the native AV valve;
- The provision prosthetic valves that can be implanted without a cardiopulmonary bypass apparatus;
- The provision prosthetic valves that can be positioned proximate a valve annulus, transvascularly; and
- The provision prosthetic valves that can be positioned proximate a valve annulus, transapically.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An adaptable prosthetic valve for modulating fluid flow through an atrioventricular (AV) valve annulus region during cardiac cycles of a heart, said AV valve annulus region comprising a plurality of AV valve annulus configurations and a plurality of AV valve annulus dimensions, said prosthetic valve comprising:

a base valve member and an internal support structure, said base valve member comprising a continuous sheet member, said base valve member comprising mammalian-based tissue from a mammalian tissue source, said base valve member comprising an internal lumen adapted to transmit fluid flow therethrough, a proximal annular engagement end and a distal end, said proximal annular engagement end being configured to engage said AV valve annulus region, said proximal annular engagement end being further configured and adapted to transition from a first proximal annular engagement end operative configuration to a second proximal annular engagement end operative configuration, and a first proximal annular engagement end operative dimension and a second proximal annular engagement end operative dimension, said first proximal annular engagement end operative configuration conforming to a first AV valve annulus region configuration of said plurality of AV valve annulus configurations, said first proximal annular engagement end operative dimension conforming to a first AV valve annulus region dimension of said plurality of AV valve annulus dimensions, said second proximal annular engagement end operative configuration conforming to a second AV valve annulus region configuration of said plurality of AV valve annulus configurations, and said second proximal annular engagement end operative dimension conforming to a second AV valve annulus region dimension of said plurality of AV valve annulus dimensions, said first proximal annular engagement end operative configuration conforming to said first AV valve annulus region configuration, said first proximal annular engagement end operative dimension conforming to said first AV valve annulus region dimension, said second proximal annular engagement end operative configuration conforming to said second AV valve annulus region configuration, and said second proximal annular engagement end operative dimension conforming to said second AV valve annulus region dimension, said proximal annular engagement end of the base valve member comprising a plurality of equally spaced ribbon members, each of said plurality of ribbon members comprising proximal and distal ends, a first edge region extending from said proximal end of each of said plurality of ribbon members to said distal end of each of said plurality of ribbon members and a second edge region extending from said proximal end of each of said plurality of ribbon members to said distal end of each of said plurality of ribbon members, said plurality of ribbon members being positioned circumferentially about said proximal annular engagement end and extending toward said distal end of said base valve member, wherein said first edge regions of said plurality of ribbon members are positioned proximate said second edge regions of said plurality of ribbon members, wherein a plurality of fluid flow modulating regions is formed between adjacent ribbons of said plurality of ribbon members, said distal ends of said plurality of ribbon members being disposed proximate each other in a joined relationship, wherein said fluid flow through said distal end of said base valve member is restricted while said fluid flow is allowed to be transmitted through said plurality of fluid flow modulating regions when in an open position, said base valve member, when said proximal annular engagement end of said base valve member is engaged to said AV valve annulus region, being configured to transition from an expanded position, wherein said base valve member receives said fluid flow therein and said fluid flow exhibits a first fluid flow pressure, to a collapsed position when said fluid flow exhibits a second fluid flow pressure, said second fluid flow pressure being lower than said first fluid flow pressure, said plurality of fluid flow modulating regions being configured to transition from an open fluid flow position when said base valve member is in said expanded position, wherein said plurality of fluid flow modulating regions allow said fluid flow to be transmitted through said base valve member, to a closed fluid flow position when said base valve member is in said collapsed position, wherein said plurality of fluid flow modulating regions restrict said fluid flow through said base valve member, said support structure comprising a base and a plurality of elongated support members having proximal and distal ends, said base being disposed proximate said distal end of said base valve member, said support structure comprising support members extending from said base to a ribbon member region distal to the proximal ends of the ribbon members, a proximal end of said support structure comprising a discontinuous, cross-linked circumferential proximal end, said plurality of elongated support members being adapted to exert an outwardly projecting retaining force on the proximal annular engagement end, whereby said support structure positions said proximal annular engagement end of said base valve member adjacent to and, thereby, in contact with said AV valve annulus region and induces said transition of said proximal annular engagement end of said base valve member from said first proximal annular engagement end operative configuration to said second proximal annular engagement end operative configuration, and said first proximal annular engagement end operative dimension to said second proximal annular engagement end operative dimension in response to a transition of said first AV valve annulus region configuration to said second AV valve annulus region configuration and said first AV valve annulus region dimension to said second AV valve annulus region dimension, wherein said proximal annular engagement end of said base valve member remains in contact with said AV valve annulus region.

2. The prosthetic valve of claim 1, wherein said mammalian tissue source is selected from the group consisting of the heart, small intestine, large intestine, stomach, lung, liver, kidney, pancreas, peritoneum, placenta, amniotic membrane, umbilical cord, bladder, prostate, and any fetal tissue from any mammalian organ.

3. The prosthetic valve of claim 2, wherein said mammalian-based tissue is devoid of xenogeneic antigens.

4. The prosthetic valve of claim 2, wherein said mammalian-based tissue comprises acellular ECM.

5. The prosthetic valve of claim 2, wherein said mammalian-based tissue comprises pericardium tissue.

6. The prosthetic valve of claim 1, wherein said mammalian-based tissue further comprises at least one exogenously added biologically active agent.

7. The prosthetic valve of claim 6, wherein said biologically active agent comprises a cell selected from the group consisting of a human embryonic stem cell, fetal cardiomyocyte, myofibroblast, and mesenchymal stem cell.

8. The prosthetic valve of claim 6, wherein said biologically active agent comprises a growth factor selected from the group consisting of a transforming growth factor-alpha (TGF-α), transforming growth factor-beta (TGF-β), fibroblast growth factor-2 (FGF-2), and vascular endothelial growth factor (VEGF).

9. The prosthetic valve of claim 1, wherein said mammalian-based tissue further comprises a pharmacological agent.

10. The prosthetic valve of claim 9, wherein said pharmacological agent comprises an agent selected from the group consisting of an antibiotic, anti-viral agent, analgesic, anti-inflammatory, anti-neoplastic, anti-spasmodic, anti-coagulant and anti-thrombotic.

11. The prosthetic valve of claim 1, wherein said support structure comprises a shape memory alloy.

12. The prosthetic valve of claim 11, wherein said shape memory alloy comprises a nickel-titanium alloy.

* * * * *